(12) United States Patent
Shin et al.

(10) Patent No.: US 11,292,798 B2
(45) Date of Patent: Apr. 5, 2022

(54) MEROCYANINE-BASED COMPOUND AND BIOMOLECULAR LABELING DYE, KIT AND CONTRAST AGENT COMPOSITION COMPRISING SAME

(71) Applicant: SFC CO., LTD., Cheongju-si (KR)

(72) Inventors: Bong-Ki Shin, Cheongju-si (KR); Jong-Tae Je, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 240 days.

(21) Appl. No.: 16/848,586

(22) Filed: Apr. 14, 2020

(65) Prior Publication Data

US 2020/0239491 A1 Jul. 30, 2020

Related U.S. Application Data

(63) Continuation of application No. PCT/KR2018/011689, filed on Oct. 2, 2018.

(30) Foreign Application Priority Data

Oct. 17, 2017 (KR) .................. 10-2017-0134842
Sep. 19, 2018 (KR) .................. 10-2018-0111943

(51) Int. Cl.
| | | |
|---|---|---|
| *A61B 5/00* | (2006.01) | |
| *A61B 8/00* | (2006.01) | |
| *A61B 10/00* | (2006.01) | |
| *C07D 491/147* | (2006.01) | |
| *A61K 49/00* | (2006.01) | |

(52) U.S. Cl.
CPC ...... *C07D 491/147* (2013.01); *A61K 49/0032* (2013.01)

(58) Field of Classification Search
CPC .................. C07D 491/147; A61K 49/0032
See application file for complete search history.

(56) References Cited

U.S. PATENT DOCUMENTS

| | | |
|---|---|---|
| 2,656,353 A | 10/1953 | Jeffreys et al. |
| 5,929,245 A | 7/1999 | Grund et al. |
| 6,048,982 A | 4/2000 | Waggoner |

FOREIGN PATENT DOCUMENTS

| | | |
|---|---|---|
| EP | 1152008 A2 | 11/2001 |
| KR | 10-2017-0009795 A | 1/2017 |

OTHER PUBLICATIONS

International Search Report issued in PCT/KR2018/011689; dated Jan. 18, 2019.

*Primary Examiner* — Michael G. Hartley
*Assistant Examiner* — Melissa J Perreira
(74) *Attorney, Agent, or Firm* — Studebaker & Brackett PC

(57) ABSTRACT

The present invention relates to: a novel merocyanine-based compound which exhibits a fluorescence signal at a visible light region of at least 380 nm, and which may be used for detecting biomolecules; and a biomolecular labeling dye, kit and contrast agent composition comprising the same.

8 Claims, 2 Drawing Sheets

MEROCYANINE-BASED COMPOUND AND BIOMOLECULAR LABELING DYE, KIT AND CONTRAST AGENT COMPOSITION COMPRISING SAME

CROSS-REFERENCE TO RELATED APPLICATIONS

This application is a continuation of International Patent Application No. PCT/KR2018/011689 filed on Oct. 2, 2018, which is based upon and claims the benefit of priority to Korean Application No. 10-2017-0134842, filed on Oct. 17, 2017 and Korean Application No. 10-2018-0111943, filed on Sep. 19, 2018. The disclosures of the above-listed applications are hereby incorporated by reference herein in their entirety.

TECHNICAL FIELD

The present invention relates to: a novel merocyanine-based compound which exhibits a fluorescence signal at a visible light region of at least 380 nm, and which may be used for detecting biomolecules; and a biomolecular labeling dye, kit and contrast agent composition comprising same.

This research was supported by a grant from the Advanced Technology Center (ATC) Program (Ser. No. 10/076,988, Development of fluorescent materials and their application technologies for molecular diagnosis) funded by the Ministry of Trade, Industry & Energy of the Republic of Korea.

BACKGROUND ART

In order to observe a biological phenomenon or contrast an organism and examine a diseased site at the cellular level in vivo and in vitro in the field of biotechnology, fluorescence dyes have been used as a means capable of visualizing the same. Although there are biomolecules which emit light independently, such as a green fluorescent protein (GFP), generally, after biological tissues or cells and biological materials at lower levels are stained with fluorescent dyes, or biological molecules such as proteins and nucleic acids are labeled with fluorescent dyes, an accompanying optical system can detect a fluorescence signal, thereby obtaining visualized data by various techniques.

As an optical analysis device which is usually used, those for diagnosis and treatment such as an in vitro diagnosis device based on a nucleic acid and protein diagnosis kit (or biochip) combined with an immunoassay or PCR analysis and statistical technology and an operating table and endoscope device for image-guided surgery are known in addition to a device for the purpose of research such as a fluorescence microscope, a confocal microscope, a flow cytometer, and a quantitative PCR system, an electrophoresis device for isolating and analysis nucleic acids and proteins, and a real-time in vivo imaging system, and new application areas and devices with higher levels of resolution and data processing capabilities are being continuously developed.

In order to apply fluorescent dyes to the field of biotechnology, those, which have low photobleaching and quenching and a high molecular extinction coefficient and high quantum efficiency when generally present in a medium in which most of the biomolecules are present, that is, an aqueous solution and are stable under various pH conditions, are preferred.

Although various fluorescent dyes have been used in various research areas, fluorescent dyes which satisfy the above-described conditions in the field of biotechnology are extremely rare. For example, fluorescent dyes having a coumarin, cyanine, BODIPY, fluorescein, rhodamine, pyrene, carbopyronin, oxazine, xanthene, thioxanthene or acridine skeleton have been commonly used.

DISCLOSURE

Technical Problem

An object of the present invention is to provide a novel merocyanine-based compound having a skeleton which is different from that of a fluorescent dye widely known in the related art as a compound that may be used widely to observe the identification of biomolecules in the optical imaging field.

Further, an object of the present invention is to provide a biomolecular labeling dye, kit and contrast agent composition including a novel merocyanine-based compound.

Technical Solution

According to an aspect of the present invention for solving the above-described technical problems, a merocyanine-based compound represented by the following Chemical Formula 1 may be provided.

[Chemical Formula 1]

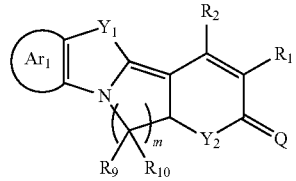

wherein, $Ar_1$ is a substituted or unsubstituted aryl or a substituted or unsubstituted heteroaryl, $Y_1$ and $Y_2$ are each independently selected from sulfur, oxygen, selenium, $NR_3$, $CR_3R_4$, $SiR_3R_4$, and —$CR_3$=$CR_4$—, Q is sulfur, oxygen, or $NR_a$, $R_1$ may be each independently selected from hydrogen, deuterium, a substituted or unsubstituted $C_1$-$C_{10}$ alkyl, a substituted or unsubstituted $C_2$-$C_{10}$ alkenyl, a substituted or unsubstituted $C_1$-$C_{10}$ haloalkyl, a halogen, cyano, a substituted or unsubstituted amino, a substituted or unsubstituted amide, carboxyl, carboxylates, a substituted or unsubstituted aryl, a substituted or unsubstituted heteroaryl, ketones (—$COR_5$), aldehydes, esters (—$COOR_5$), a -L-X functional group, and a -L-Z functional group, and $R_a$ and $R_2$ to $R_4$ may be each independently selected from hydrogen, deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones (—$COR_5$), aldehydes, esters (—$COOR_5$), acyl chloride, sulfonic acid, sulfonates, a -L-X functional group, and a -L-Z functional group.

Here, when $R_1$, $R_2$, $R_3$, or $R_4$ is a ketone group (—$COR_5$) or an ester group (—$COOR_5$), $R_5$ may be selected from a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted $C_1$-$C_{10}$ haloalkyl, a substituted or unsubstituted heteroaryl, and a substituted or unsubstituted $C_1$-$C_{10}$ aminoalkyl.

$R_9$ and $R_{10}$ may be selected from hydrogen and a substituted or unsubstituted alkyl, and $R_9$ and $R_{10}$ may be bonded to each other to form a four-membered, five-membered, or six-membered hydrocarbon ring.

In the -L-X functional group, L is a linker selected from 1-20 atoms selected from carbon, nitrogen, oxygen, and sulfur, —NHCOO—, —CONH—, —$CH_2NH$—, —$CH_2NR_6$—, —COO—, —$SO_2NH$—, —HN—C(=NH)—NH—, —$NR_6$—, —($CH_2$—$CH_2$—O—)$_p$—, —CH=CH—, —C≡C—, —Ar—, and —CO—Ar—$NR_6$—, $R_6$ is selected from hydrogen, a substituted or unsubstituted $C_1$-$C_6$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_6$ alkoxy, and a substituted or unsubstituted $C_1$-$C_6$ haloalkyl, Ar is an aryl or a heteroaryl, p is an integer from 1 to 100, and X is a reactive group selected from carboxyl, succinimidyl ester, sulfo-succinimidyl ester, isothiocyanate, maleimide, haloacetamide, hydrazide, vinyl sulphone, dichlorotriazine, phosphoramidite, alkyl halides, acyl halides, carbohydrazide, hydroxylamine, ketones, alkynes, azide, aliphatic and aromatic amines, sulfotetrafluorophenyl ester, sulfodichlorophenyl ester, carbonyl azide, sulfonyl chloride, sulfonyl fluoride, boronic acid, isocyanate, a halogen-substituted triazine, a halogen-substituted pyridine, a halogen-substituted diazine, tetrafluorophenyl ester, imido ester, azidonitrophenyl, glyoxal, and aldehyde.

In the -L-Z functional group, L is a linker selected from 1-20 atoms selected from carbon, nitrogen, oxygen, and sulfur, —NHCOO—, —CONH—, —$CH_2NH$—, —$CH_2NR_6$—, —COO—, —$SO_2NH$—, —HN—C(=NH)—NH—, —$NR_6$—, —($CH_2$—$CH_2$—O—)$_p$—, —CH=CH—, —C≡C—, —Ar—, and —CO—Ar—$NR_6$—, $R_6$ is selected from hydrogen, a substituted or unsubstituted $C_1$-$C_6$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_6$ alkoxy, and a substituted or unsubstituted $C_1$-$C_6$ haloalkyl, Ar is an aryl, p is an integer from 1 to 100, and Z is a fluorophore capable of generating a fluorescence signal.

In an exemplary embodiment, Z may be coumarins, cyanine, BODIPY, fluoresceins, rhodamines, pyrenes, carbopyronin, oxazines, xanthenes, thioxanthene or acridines, or Chemical Formula 1, and further, when $R_1$, $R_2$, $R_3$, $R_4$, $R_5$, or $R_6$ is substituted, any carbon or terminal carbon in the functional group may be substituted with at least one selected from sulfonic acid, sulfonates, carboxylic acids, carboxylates, phosphoric acid, phosphates, alkyls, heteroaryl, polyalkylene oxides, quaternary ammonium salts, esters, and amides.

Here, a heteroaryl may include a salt form having a (+) charge by substituting a heteroatom in the heteroaryl with a specific functional group, like pyridinium or quinolinium.

Further, m is preferably an integer from 1 to 3.

According to another aspect of the present invention, a biomolecular labeling dye including a merocyanine-based compound represented by Chemical Formula 1 may be provided.

In addition, according to still another aspect of the present invention, a biomolecular labeling kit including a merocyanine-based compound represented by Chemical Formula 1 may be provided.

Furthermore, according to yet another aspect of the present invention, a contrast agent composition including a merocyanine-based compound represented by Chemical Formula 1 may be provided.

Advantageous Effects

The novel merocyanine-based compound according to the present invention can be bonded to a biomolecule to exhibit a fluorescence signal at a visible light region of at least 380 nm. Based on this, the merocyanine-based compound according to the present invention can be usefully used as a biomolecular labeling dye, a biomolecular labeling kit, a contrast agent composition, and the like.

MODES OF THE INVENTION

Figure 1:
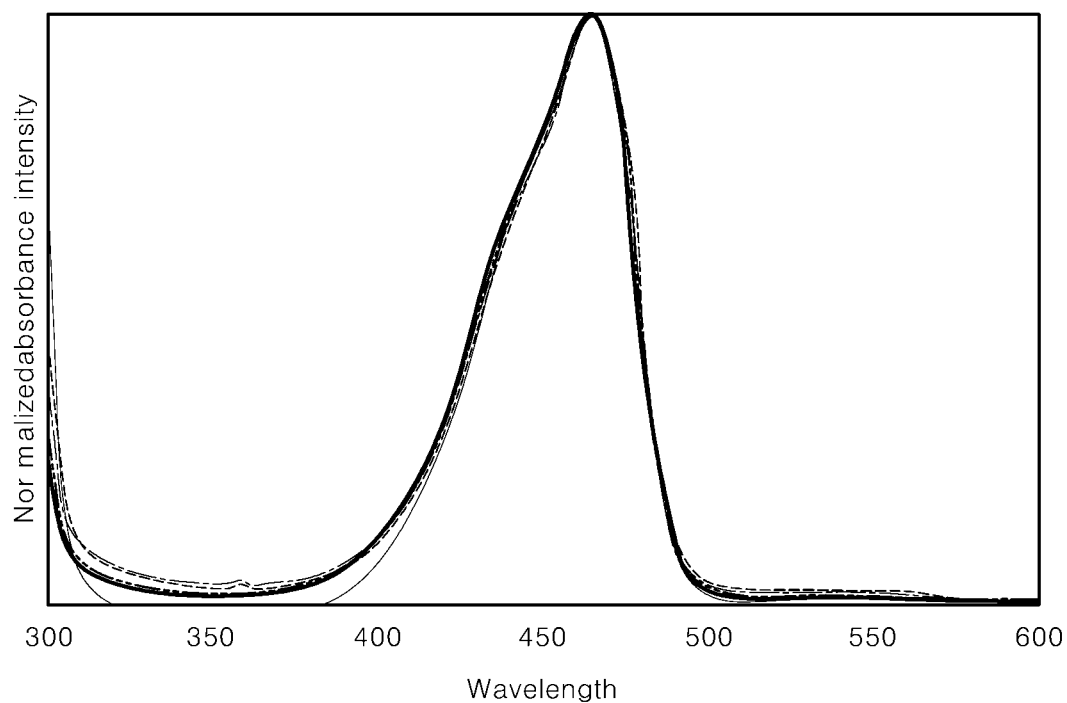
FIG. 1 illustrates absorption spectra after labeling Goat Anti-Mouse IgG with a merocyanine-based compound (Compound 2) according to an exemplary embodiment of the present invention.

In order to more easily understand the present invention, specific terms are defined herein for convenience. Unless otherwise defined herein, scientific terms and technical terms used in the present invention may have the meaning commonly understood by a person with ordinary skill in the art.

Further, unless specially indicated in the context, terms in a singular form also include the plural forms thereof, and terms in a plural form may also include the singular forms thereof.

Novel Merocyanine-Based Compound

According to an aspect of the present invention, a merocyanine-based compound represented by the following Chemical Formula 1 may be provided.

[Chemical Formula 1]

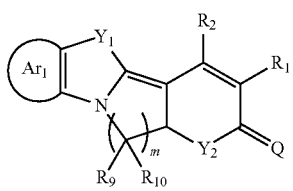

wherein, $Ar_1$ is a substituted or unsubstituted aryl or a substituted or unsubstituted heteroaryl, and $Y_1$ and $Y_2$ may be each independently selected from sulfur, oxygen, selenium, $NR_3$, $CR_3R_4$, $SiR_3R_4$, and $-CR_3=CR_4-$. In an exemplary embodiment, when $Y_1$ or $Y_2$ is $CR_3R_4$, $R_3$ and $R_4$ may be bonded to each other to form a four-membered, five-membered, or six-membered ring.

Further, Q may be sulfur, oxygen, or $NR_a$.

$R_1$ may be each independently selected from hydrogen, deuterium, a substituted or unsubstituted $C_1$-$C_{10}$ alkyl, a substituted or unsubstituted $C_2$-$C_{10}$ alkenyl, a substituted or unsubstituted $C_1$-$C_{10}$ haloalkyl, a halogen, cyano, a substituted or unsubstituted amino, a substituted or unsubstituted amide, carboxyl, carboxylates, a substituted or unsubstituted aryl, a substituted or unsubstituted heteroaryl, ketones ($-COR_5$), aldehydes, esters ($-COOR_5$), a -L-X functional group, and a -L-Z functional group.

Further, $R_a$ and $R_2$ to $R_4$ may be each independently selected from hydrogen, deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones ($-COR_5$), aldehydes, esters ($-COOR_5$), acyl chloride, sulfonic acid, sulfonates, a -L-X functional group, and a -L-Z functional group.

Here, when $R_1$, $R_2$, $R_3$, or $R_4$ is a ketone group ($-COR_5$) or an ester group ($-COOR_5$), $R_5$ may be selected from a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted $C_1$-$C_{10}$ haloalkyl, a substituted or unsubstituted heteroaryl, and a substituted or unsubstituted $C_1$-$C_{10}$ aminoalkyl.

$R_9$ and $R_{10}$ may be selected from hydrogen and a substituted or unsubstituted alkyl, and $R_9$ and $R_{10}$ may be bonded to each other to form a four-membered, five-membered, or six-membered hydrocarbon ring.

when $R_1$, $R_2$, $R_3$, or $R_4$ is an alkenyl or alkynyl, it may be in a form directly bonded by an $sp^2$-hybridized carbon of the alkenyl or an sp-hybridized carbon of the alkynyl or in a form indirectly bonded by an $sp^a$-hybridized carbon of an alkyl which is bonded to the $sp^2$-hybridized carbon of the alkenyl or the sp-hybridized carbon of the alkynyl.

As used herein, a $C_a$-$C_b$ functional group refers to a functional group having a to b carbon atoms. For example, a $C_a$-$C_b$ alkyl refers to a saturated aliphatic group having a to b carbon atoms, which includes a straight chain alkyl, a branched alkyl, and the like. The straight chain or branched alkyl has 10 or less (for example, a $C_1$-$C_{10}$ straight chain and a $C_3$-$C_{10}$ branched chain), preferably 4 or less, and more preferably 3 or less carbon atoms.

Specifically, the alkyl may be methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl.

Further, as used herein, the alkoxy refers to both an —O-(alkyl) group and an —O— (unsubstituted cycloalkyl) group, and is a straight chain or branched hydrocarbon having one or more ether groups and 1 to 10 carbon atoms.

Specific examples thereof include methoxy, ethoxy, propoxy, isopropoxy, n-butoxy, tert-butoxy, sec-butoxy, n-pentoxy, n-hexoxy, 1,2-dimethylbutoxy, cyclopropyloxy, cyclobutyloxy, cyclopentyloxy, cyclohexyloxy, and the like, but are not limited thereto.

Further, as used herein, the halogen refers to fluoro (—F), chloro (—Cl), bromo (—Br), or iodo (—I), and the haloalkyl refers to an alkyl substituted with the above-described halogen. For example, the halomethyl refers to a methyl ($-CH_2X$, $-CHX_2$, or $-CX_3$) in which at least one of hydrogens of a methyl is replaced with a halogen.

As used herein, the aralkyl collectively refers to $-(CH_2)_n$ Ar as a functional group in a form where an aryl is substituted with carbon of an alkyl. Examples of the aralkyl include benzyl ($-CH_2C_6H_5$), phenethyl ($-CH_2CH_2C_6H_5$), or the like.

In the -L-X functional group, L is a linker selected from 1-20 atoms selected from carbon, nitrogen, oxygen, and sulfur, —NHCOO—, —CONH—, —CH$_2$NH—, —CH$_2$NR$_6$—, —COO—, —SO$_2$NH—, —HN—C(=NH)—NH—, —NR$_6$—, —(CH$_2$—CH$_2$—O—)$_p$—, —CH=CH—, —C≡C—, —Ar—, and —CO—Ar—NR$_6$—, $R_6$ is selected from hydrogen, a substituted or unsubstituted $C_1$-$C_6$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_6$ alkoxy, and a substituted or unsubstituted $C_1$-$C_6$ haloalkyl, Ar is an aryl or a heteroaryl, and p is an integer from 1 to 100.

Non-limiting examples of X corresponding to a reactive group include carboxyl, succinimidyl ester, sulfo-succinimidyl ester, isothiocyanate, maleimide, haloacetamide, hydrazide, vinyl sulphone, dichlorotriazine, phosphoramidite, alkyl halides, acyl halides, carbohydrazide, hydroxylamine, ketones, alkynes, azide, aliphatic and aromatic amines, sulfotetrafluorophenyl ester, sulfodichlorophenyl ester, carbonyl azide, sulfonyl chloride, sulfonyl fluoride, boronic acid, isocyanate, a halogen-substituted triazine, a halogen-substituted pyridine, a halogen-substituted diazine, tetrafluorophenyl ester, imido ester, azidonitrophenyl, glyoxal, aldehydes, and the like.

In the -L-Z functional group, L is a linker which is the same as L of the -L-X functional group, and Z is a fluorophore capable of generating a fluorescence signal.

In an exemplary embodiment, Z may be coumarins, cyanine, BODIPY, fluoresceins, rhodamines, pyrenes, carbopyronin, oxazines, xanthenes, thioxanthene or acridines, or Chemical Formula 1.

When Z has a structure of Chemical Formula 1, the linker L may be linked to $R_1$, $R_2$, $R_3$, $R_4$, $R_5$, or $Ar_1$ of Chemical Formula 1, which corresponds to Z of a -L-Z functional group or may replace $R_1$, $R_2$, $R_3$, $R_4$, or $R_5$.

The merocyanine-based compounds according to various exemplary embodiments of the present invention can be bonded to a target biomolecule through the above-described reactive group to label the target biomolecule.

Here, the above-described reactive groups are functional groups capable of reacting with a functional group such as an amino group, an imino group, a thiol group, or a hydroxyl group of a target biomolecule, and may form a covalent bond such as an amide bond, an imide bond, a urethane bond, an ester bond, or a guanidine bond between a cyanine compound and the target biomolecule.

Furthermore, a reactive group (X) may be bonded to a main skeleton of a merocyanine-based compound via a linker (L) to alleviate the steric hindrance between the biomolecule and the merocyanine-based compound, and accordingly, it is possible to improve the labeling ratio for a biomolecule such as a nucleic acid, a protein, and a carbohydrate, which has a complex structure.

Further, when $R_1$, $R_2$, $R_3$, $R_4$, $R_5$, or $R_6$ is substituted, any carbon or terminal carbon in the functional group may be substituted with at least one selected from sulfonic acid, sulfonates, carboxylic acids, carboxylates, phosphoric acid, phosphates, alkyls, heteroaryls, polyalkylene oxides, quaternary ammonium salts, esters, and amides, and m is an integer from 1 to 3.

Here, a polyalkylene oxide may be further substituted, if necessary, as long as characteristics of the polymer are maintained. For example, the substitution may be a chemical bond for increasing or decreasing the chemical or biological stability of the polymer. As a specific example, any carbon or terminal carbon in the polyalkylene oxide may be substituted with hydroxyl, an alkyl ether (methyl ether, ethyl ether, propyl ether, and the like), carboxymethyl ether, carboxyethyl ether, benzyl ether, dibenzylmethylene ether, or dimethylamine. In an exemplary embodiment, the polyalkylene oxide may be a polyalkylene oxide (mPEG) terminated with methyl ether, and here, the mPEG is represented by a chemical formula of $-(CH_2CH_2O)_nCH_3$, and the size of the mPEG may vary depending on the size of n corresponding to the number of ethylene glycol repeating units.

Further, a merocyanine-based compound represented by Chemical Formula 1 may have a structure further including counter ions. The counter ion is an organic or inorganic anion, and may be appropriately selected in consideration of solubility and stability of the merocyanine compound, and the like.

Examples of the counter ion of the merocyanine-based compound according to an exemplary embodiment of the present invention include an inorganic acid anion such as a phosphoric acid hexafluoride ion, a halogen ion, a phosphoric acid ion, a perchloric acid ion, a periodic acid ion, an antimony hexafluoride ion, a tartaric acid hexafluoride ion, a fluoroboric acid ion and a tetrafluoride ion and an organic acid ion such as a thiocyanic acid ion, a benzenesulfonic acid ion, a naphthalenesulfonic acid ion, a p-toluenesulfonic acid ion, an alkylsulfonic acid ion, a benzenecarboxylic acid ion, an alkylcarboxylic acid ion, a trihaloalkylcarboxylic acid ion, an alkylsulfonic acid ion, a trihaloalkylsulfonic acid ion, and a nicotinic acid ion. In addition, a metal compound ion such as bisphenylditol, thiobisphenol chelate and bisdiol-α-diketone, a metal ion such as sodium and potassium, and quaternary ammonium salts may also be selected as the counter ion.

When $Ar_1$ is substituted, any carbon in the functional group may be substituted with at least one selected from deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, nitro, a substituted or unsubstituted sulfonamide, polyalkylene oxides, carboxyl, carboxylates, a substituted or unsubstituted aryl, a substituted or unsubstituted heteroaryl, a substituted or unsubstituted aralkyl, quaternary ammonium, phosphoric acid, phosphates, ester ($-COOR_5$), acyl chloride, sulfonic acid, sulfonates, a -L-X functional group, and a -L-Z functional group.

Furthermore, among functional groups substituted in $Ar_1$, substituents adjacent to each other may be bonded to each other to form a four-membered, five-membered, or six-membered ring.

More specifically, the merocyanine-based compound represented by Chemical Formula 1 may be represented by the following Chemical Formulae 2 to 4.

[Chemical Formula 2]

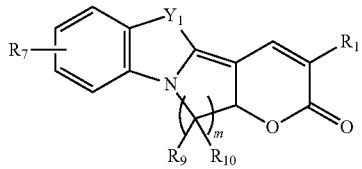

[Chemical Formula 3]

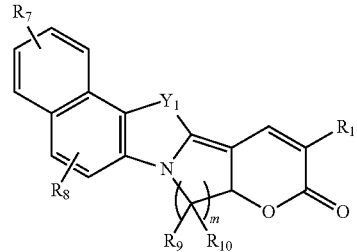

[Chemical Formula 4]

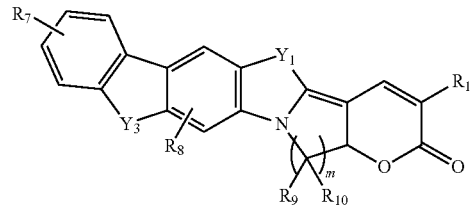

wherein, $R_7$ and $R_8$ are each independently selected from hydrogen, deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, nitro, a substituted or unsubstituted sulfonamide, polyalkylene oxides, carboxyl, carboxylates, a substituted or unsubstituted aryl, a substituted or unsubstituted heteroaryl, a substituted or unsubstituted aralkyl, quaternary ammonium, phosphoric acid, phosphates, ester (—COOR$_5$), acyl chloride, sulfonic acid, sulfonates, a -L-X functional group, and a -L-Z functional group, and Y$_3$ is sulfur, oxygen, selenium, NR$_3$, CR$_3$R$_4$, SiR$_3$R$_4$, or —CR$_3$=CR$_4$—.

According to an exemplary embodiment of the present invention, specific examples of the merocyanine-based compound represented by Chemical Formulae 1 to 4 are as follows.

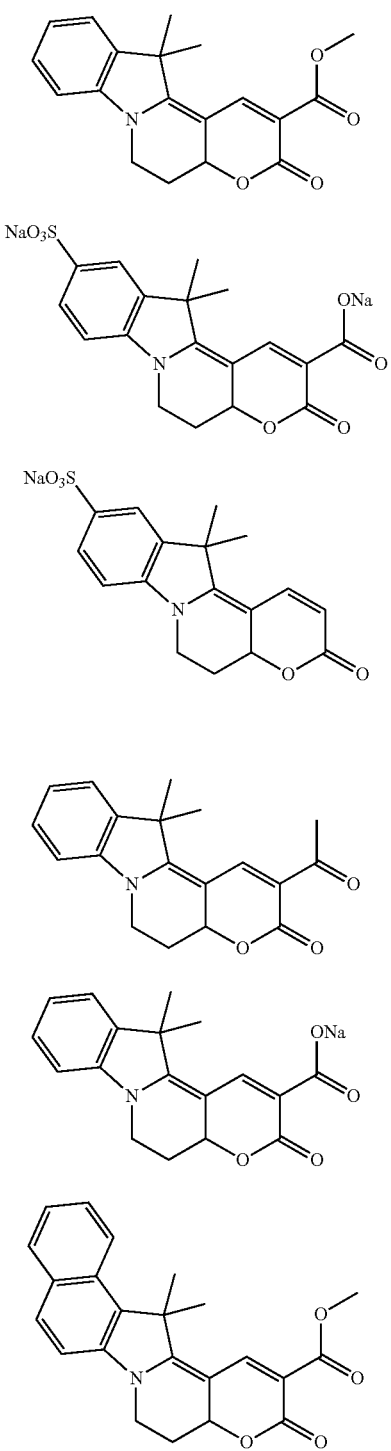

[Compound 1]

[Compound 2]

[Compound 3]

[Compound 4]

[Compound 5]

[Compound 6]

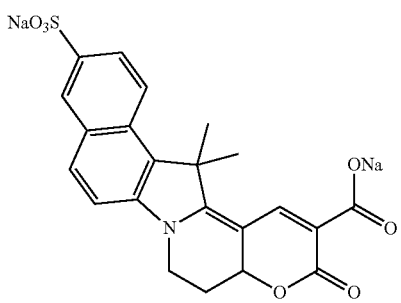

[Compound 7]

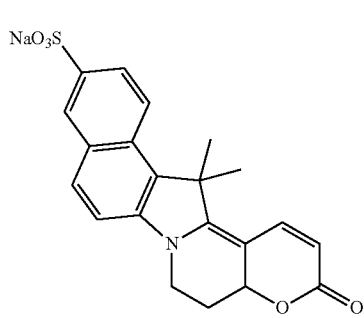

[Compound 8]

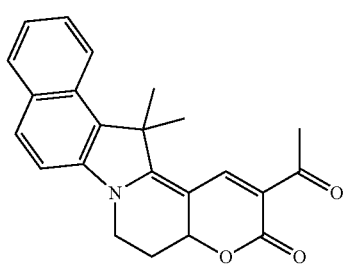

[Compound 9]

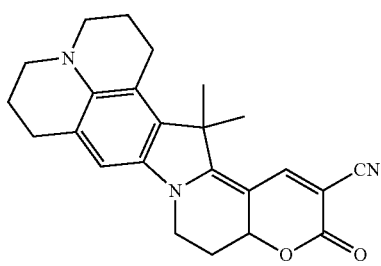

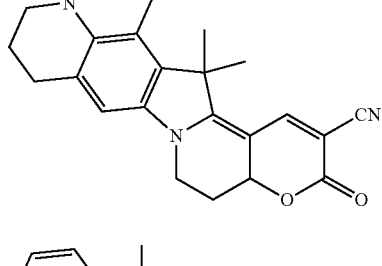

[Compound 10]

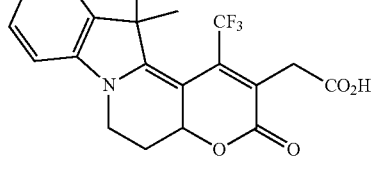

[Compound 11]

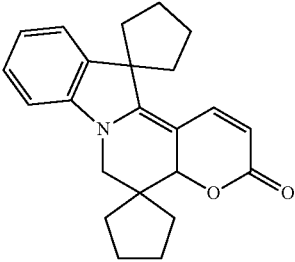

[Compound 12]

[Compound 13]
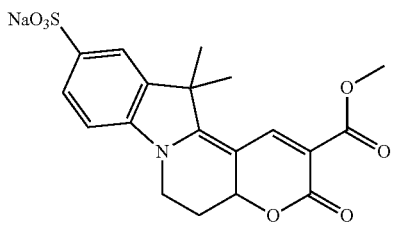
[Compound 14]
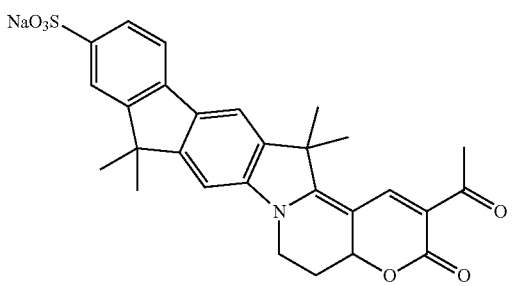
[Compound 15]
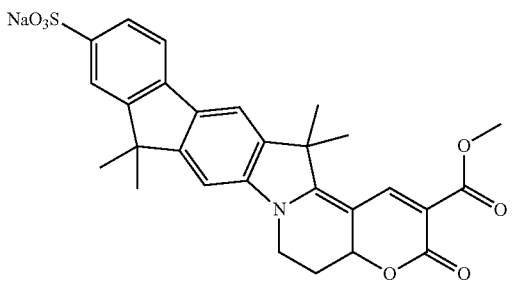
[Compound 16]
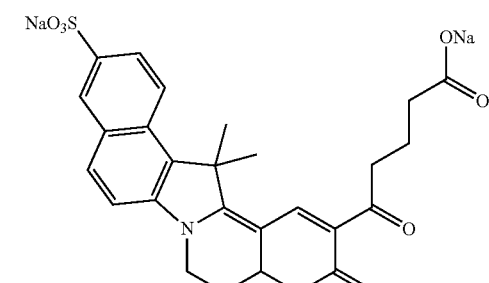
[Compound 17]
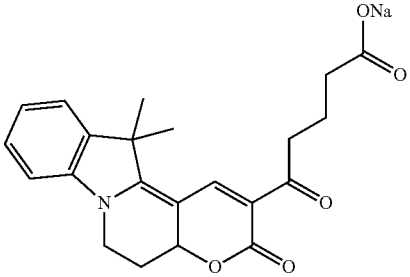
[Compound 18]
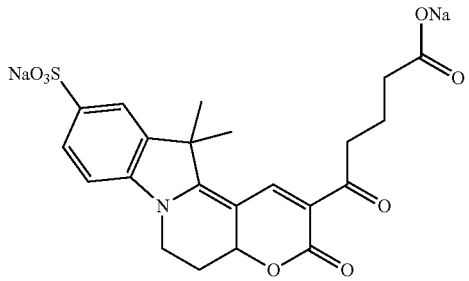
[Compound 19]
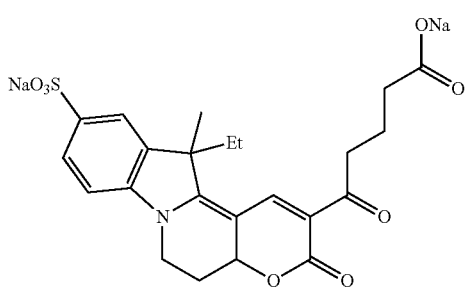
[Compound 20]
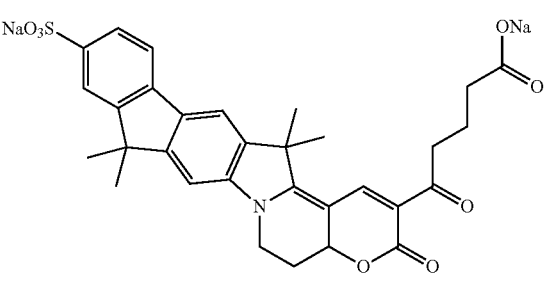
[Compound 21]
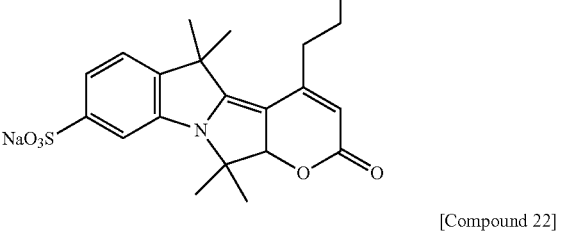
[Compound 22]
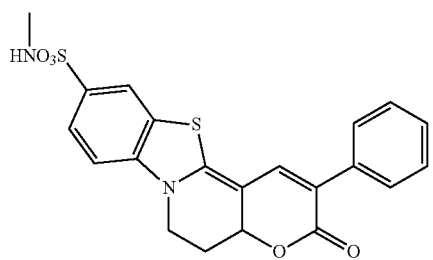
[Compound 23]
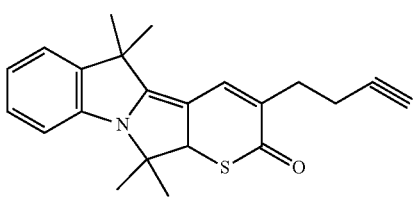

-continued
[Compound 24]
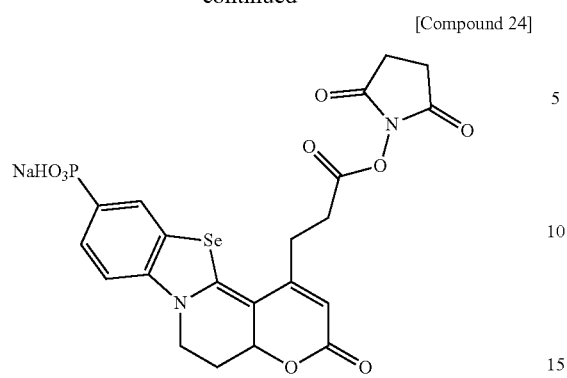
[Compound 25]
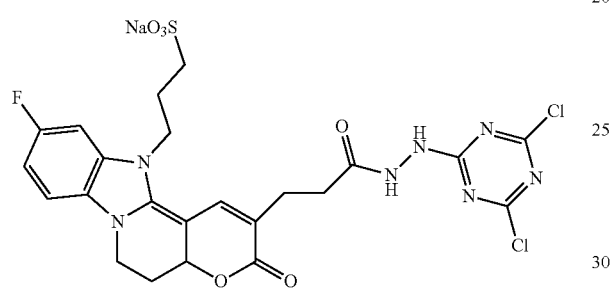
[Compound 26]
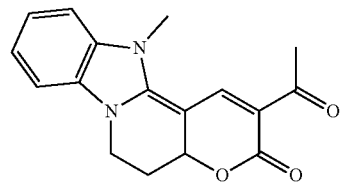
[Compound 27]
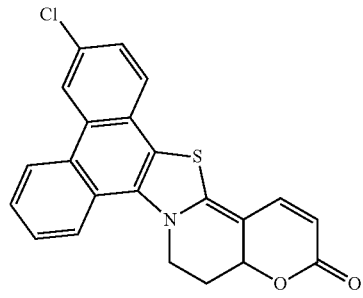
[Compound 28]
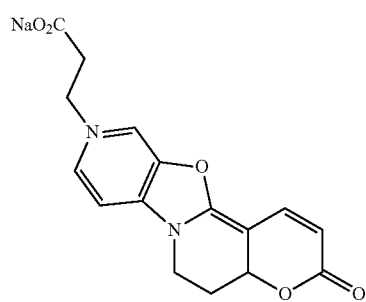
[Compound 29]
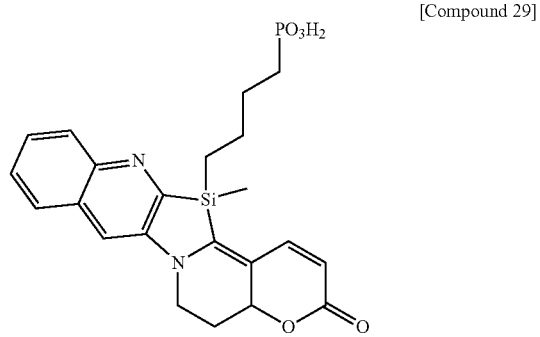
[Compound 30]
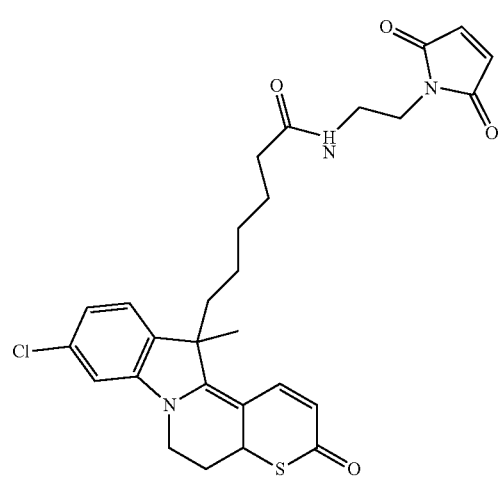
[Compound 31]
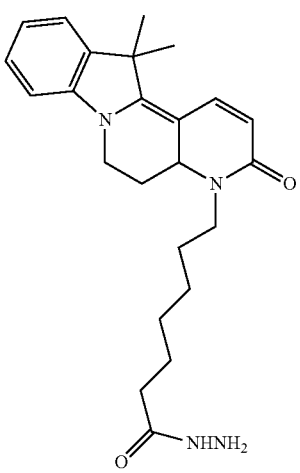

-continued
[Compound 32]
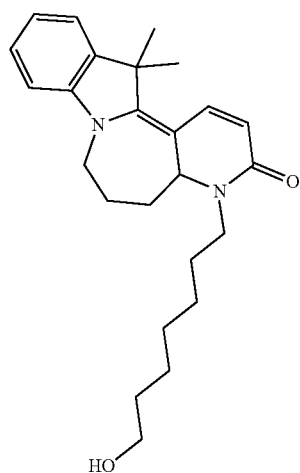
[Compound 33]
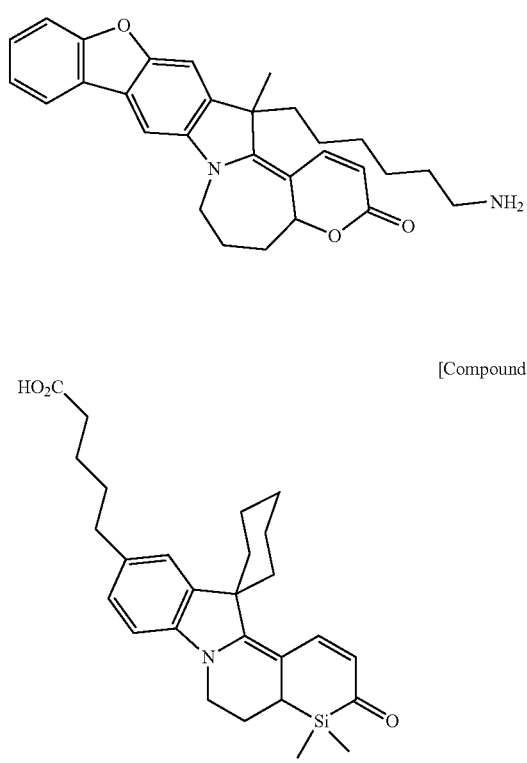
[Compound 34]
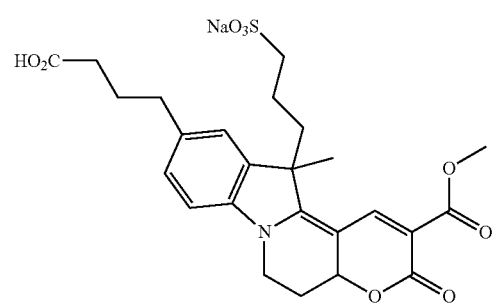
[Compound 35]
-continued
[Compound 36]
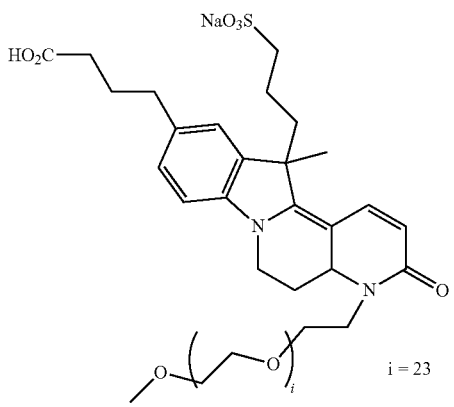
[Compound 37]
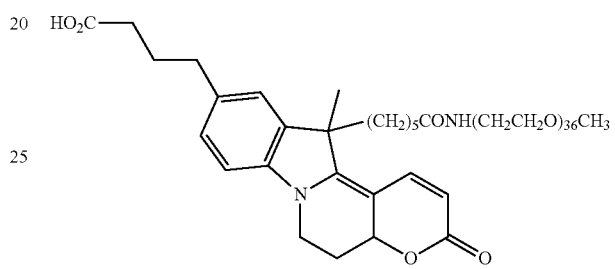
[Compound 38]
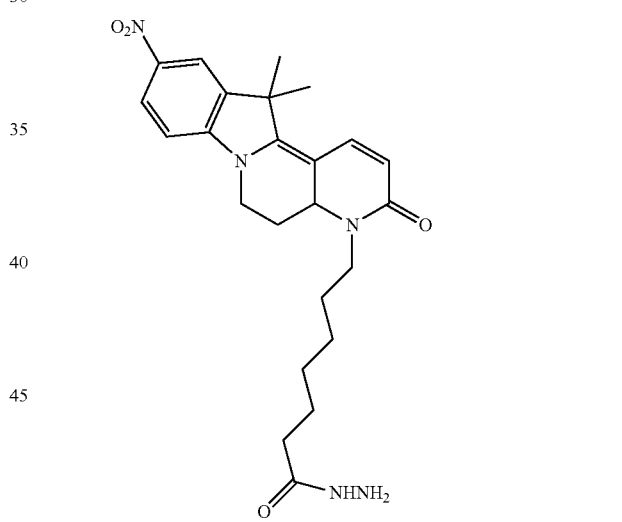
[Compound 39]
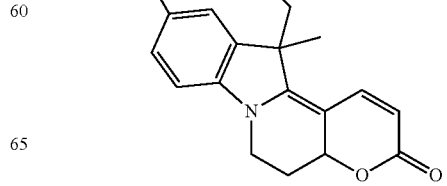

-continued
[Compound 40]
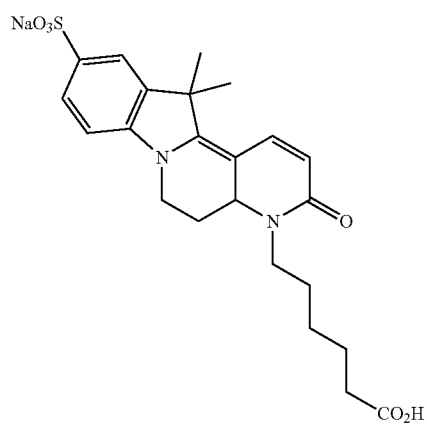
[Compound 41]
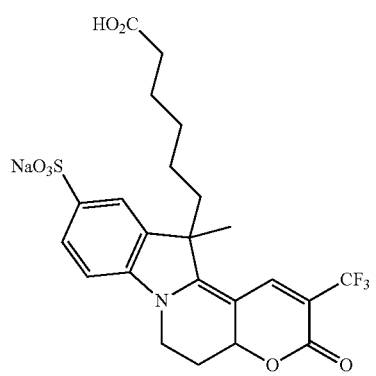
[Compound 42]
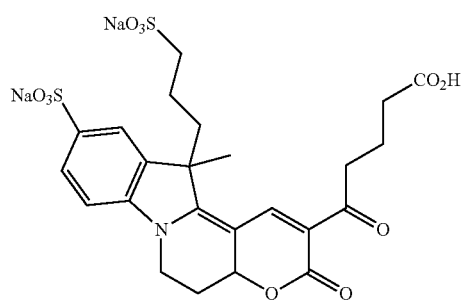
[Compound 43]
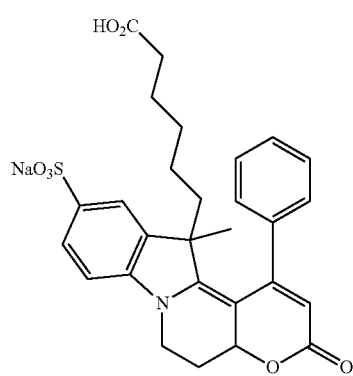
[Compound 44]
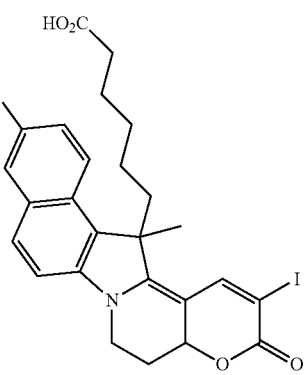
[Compound 45]
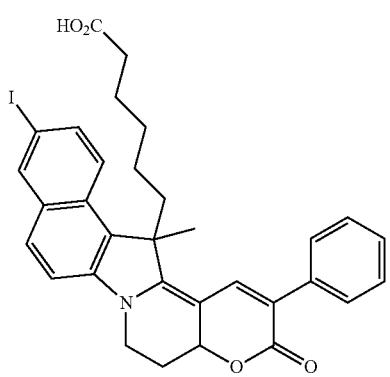
[Compound 46]
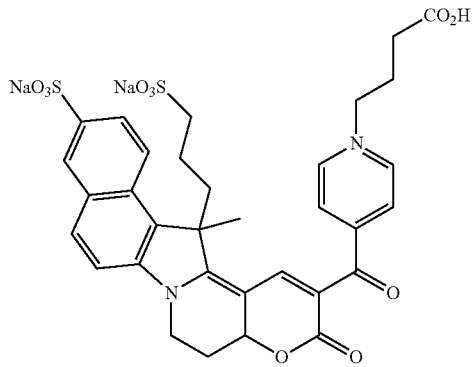
[Compound 47]
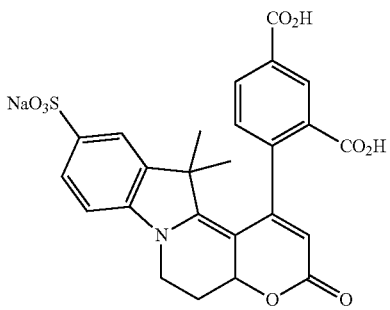

-continued
[Compound 48]
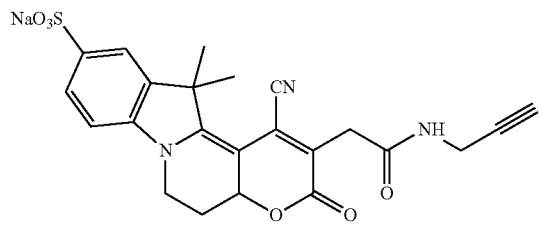
[Compound 49]
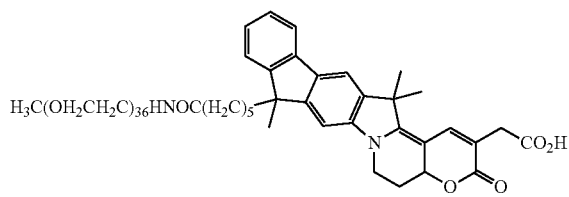
[Compound 50]
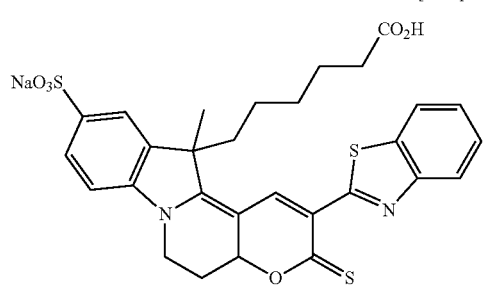
[Compound 51]
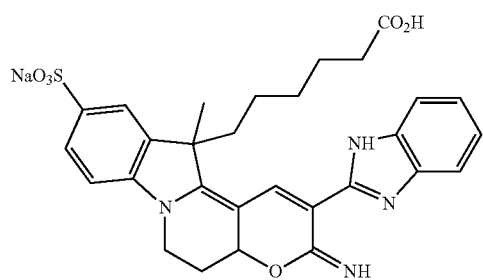
[Compound 52]
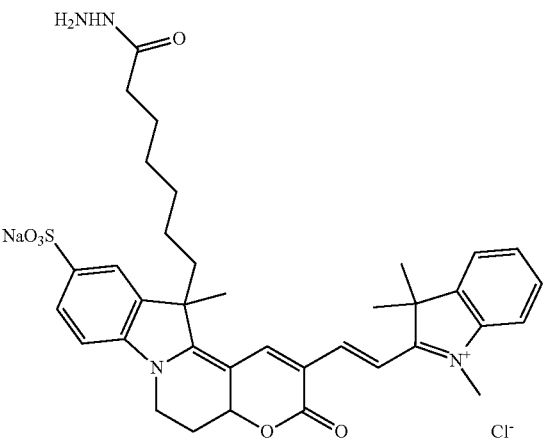
-continued
[Compound 53]
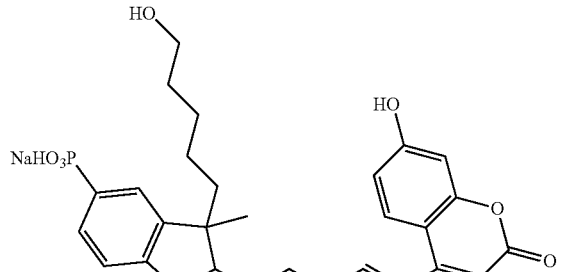
[Compound 54]
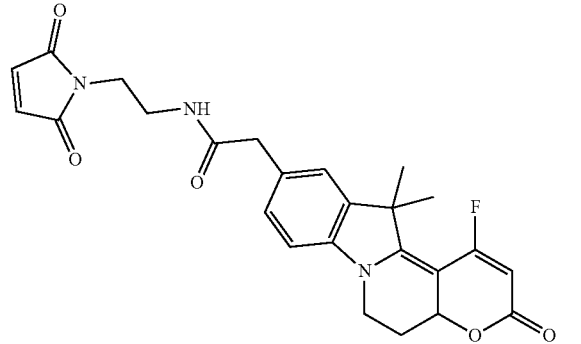
[Compound 55]
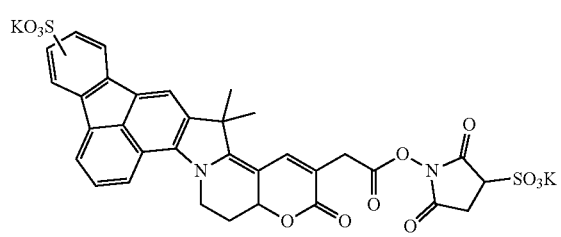
[Compound 56]
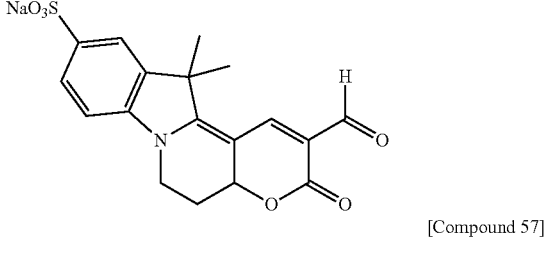
[Compound 57]
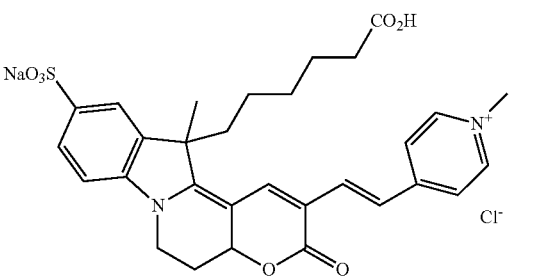

[Compound 58]

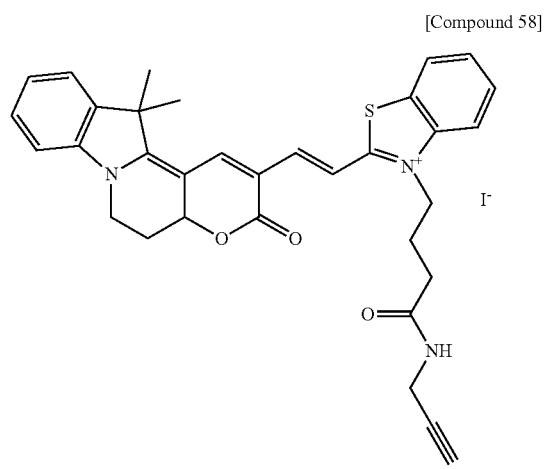

[Compound 59]

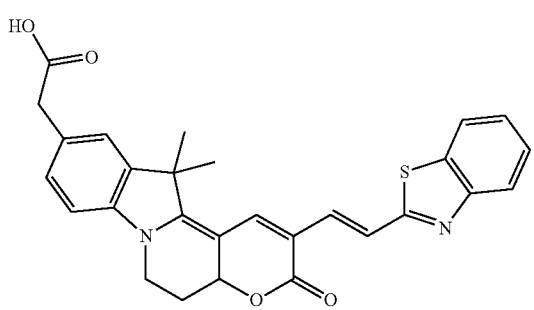

[Compound 60]

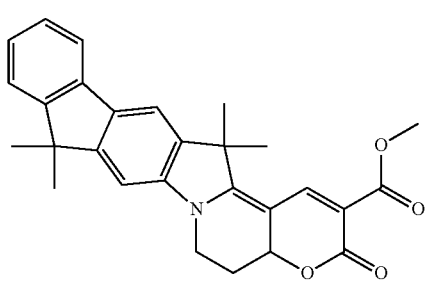

[Compound 61]

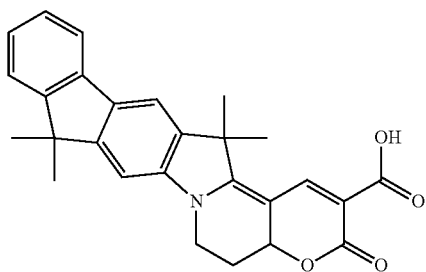

[Compound 62]

[Compound 63]

[Compound 64]

[Compound 65]

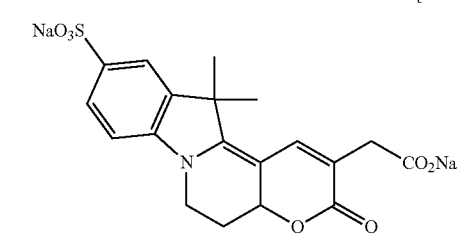

A biomolecule to be targeted by merocyanine-based compounds according to various exemplary embodiments of the present invention may be at least one selected from antibodies, lipids, proteins, carbohydrates, and nucleic acids (including nucleotides).

Specific examples of the lipids include fatty acids, phospholipids, lipopolysaccharides, and the like, and specific examples of the carbohydrates include monosaccharides, disaccharides, and polysaccharides (for example, dextran).

In this case, the biomolecule is a functional group for reacting with any functional group of a merocyanine-based compound represented by Chemical Formulae 1 to 4 or with a reactive group bonded to the merocyanine-based compound, and may include at least one selected from amino, sulfhydryl, carbonyl, hydroxyl, carboxyl, phosphate, and thiophosphate or have a derivative form thereof.

Further, the biomolecule may be an oxy or dioxy polynucleic acid which includes at least one selected from amino, sulfhydryl, carbonyl, hydroxyl, carboxyl, phosphate, and thiophosphate or have a derivative form thereof.

Furthermore, the merocyanine-based compounds according to various exemplary embodiments of the present invention may be used to label a drug, a hormone (including a receptor ligand), a receptor, an enzyme or enzyme substrate, a cell, a cell membrane, a toxin, a microorganism, a nanobio material (polystyrene microsphere, and the like), or the like, which includes at least one selected from amino, sulfhydryl, carbonyl, hydroxyl, carboxyl, phosphate, and thiophosphate, in addition to the biomolecule.

Biomolecular Labeling Dye, Kit and Contrast Agent Composition

According to another aspect of the present invention, it is possible to provide a biomolecular labeling dye, kit and contrast agent composition including at least one selected from the merocyanine-based compound represented by Chemical Formulae 1 to 4.

Further, the biomolecular labeling kit may further include an enzyme for a reaction with a target biomolecule, a solvent (buffer, and the like), other reagents, and the like, if necessary.

Here, as the solvent, it is possible to use a buffer selected from the group consisting of a phosphate buffer, a carbonate buffer, and a Tris buffer, an organic solvent selected from dimethyl sulfoxide, dimethylformamide, dichloromethane, methanol, ethanol, and acetonitrile, water, or the like, and solubility can be adjusted by introducing various functional groups into a cyanine-based compound according to the type of solvent.

In addition, the contrast agent composition according to exemplary embodiments may further a pharmaceutically acceptable carrier in addition to the merocyanine-based compound represented by Chemical Formulae 1 to 4 to be orally or parenterally administered.

Specific examples of the pharmaceutically acceptable carrier include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like.

Hereinafter, a method for detecting a biomolecule using the above-described biomolecular labeling dye or biomolecular labeling kit will be described.

Method for Detecting Biomolecule Using Biomolecular Labeling Dye

As a method for labeling a biomolecule with the merocyanine-based compound represented by Chemical Formulae 1 to 4, a detection method for measuring fluorescence of a solid or semi-solid state biomolecule may be applied to the detection of all possible biomolecules.

A detection method which is highly sensitive, chemically stable, and excellent in operability may be provided using a merocyanine-based compound instead of a fluorescent dye in the related art.

According to various exemplary embodiments of the present invention, it is possible to realize a method for labeling a biomolecule by directly reacting the merocyanine-based compound with a target biomolecule or labeling a biomolecule by reacting a probe labeled with the merocyanine-based compound with a target biomolecule.

In addition, a method for detecting a biomolecule using a target-specific interaction may also be realized by introducing an appropriate reactive group into the merocyanine-based compound according to the type of target biomolecule.

Furthermore, a method for identifying a biomolecule labeled with the merocyanine-based compound may also be realized.

DNA Microarray Method

In a DNA microarray method, while a target nucleic acid to be detected is reacted with a dye and labeled, fluorescence of the target nucleic acid is measured by preparing a single-stranded probe nucleic acid having a base sequence complementary to the target nucleic acid and hybridizing the target nucleic acid denatured into single strands and the probe nucleic acid on a substrate.

As the probe nucleic acid immobilized on a substrate in this detection method, it is possible to use a probe nucleic acid prepared by amplifying a library of cDNA such as cDNA, a library of a genome, or all genomes as a template with a PCR method, when the expression of a gene is examined.

Further, it is possible to use a probe nucleic acid by which various oligonucleotides corresponding to a mutation based on the standard sequence as already known are synthesized, when a mutation of a gene and the like are examined.

As the immobilization of the probe nucleic acid on the substrate, an appropriate method may be selected depending on the type of nucleic acid or the type of substrate. For example, it is also possible to use a method of performing electrostatic bonding to a substrate surface-treated with a cation such as polylysine using a charge of DNA.

Meanwhile, a target nucleic acid labeled with a labeling dye is prepared by mixing the target nucleic acid denatured into single strands with the labeling dye and reacting the resulting mixture. It is preferred to set the reaction temperature and the reaction time at room temperature to 60° C. and 2 to 48 hours, respectively.

Subsequently, the labeled target nucleic acid is dropped on the substrate and hybridized.

It is preferred to perform hybridization within the ranges of room temperature to 70° C. and 2 to 48 hours. By hybridization, a target nucleic acid having a base sequence complementary to a probe nucleic acid is selectively bonded to the probe nucleic acid. Thereafter, the substrate is washed and dried at room temperature.

Subsequently, the fluorescence intensity of the dried substrate surface is measured by a fluorescence laser scanner method. The level of gene expression may be monitored by fluorescence intensity.

Meanwhile, for the hybridization, a method of immobilizing a probe nucleic acid on a substrate has been described, but a method of immobilizing a target nucleic acid labeled with a dye in advance on a substrate and dropping the probe nucleic acid on the substrate may also be used.

PCR Method

In a PCR method, fluorescence of a target nucleic acid is measured by labeling a probe complementary to a base sequence of the target nucleic acid to be detected with a dye, reacting the probe with the target nucleic acid before or after amplifying the target nucleic acid.

Specifically, an elongation reaction of the target nucleic acid is performed by an enzyme (a DNA polymerase, an RNA polymerase), and in this case, the enzyme recognizes a double-stranded nucleic acid sequence formed by a primer consisting of the target nucleic acid and the oligonucleotide, and the elongation reaction is performed from the recognized position, and only a desired gene region is amplified.

When the enzyme synthesizes a nucleic acid, a synthesis reaction is performed using nucleotides (dNTP, NTP) as raw materials.

In this case, when a nucleotide having a dye is mixed with a typical nucleotide (dNTP, NTP) at an arbitrary ratio, a nucleic acid into which the dye having the ratio is introduced may be synthesized.

Further, a nucleic acid into which a labeling dye is introduced may also be synthesized by introducing a nucleotide having an amino group at an arbitrary ratio by PCR, and then bonding the labeling dye to the nucleotide.

When the enzyme synthesizes a nucleic acid, a synthesis reaction is performed using nucleotides as raw materials, and when a product obtained by replacing a 3' OH of the nucleotide with H in this case is used, the extension reaction of the nucleic acid is no longer performed, and the reaction is terminated at the time point.

This nucleotide, dideoxynucleotide triphosphate (ddNTP), is called a terminator.

When a nucleic acid is synthesized by mixing a terminator with a typical nucleotide, the terminator is introduced at a certain probability and the reaction is terminated, so that nucleic acids with various lengths are synthesized.

When these are subjected to size separation by gel electrophoresis, DNAs are arranged in order of length. Here, when the terminator is labeled with a different labeling dye for each type of base, a tendency depending on each base is observed at the end point (3' end) of the synthesis reaction, so that the base sequence information of the target nucleic acid may be obtained by reading fluorescence information beginning with the labeling dye labeled to the terminator.

Further, the nucleic acid may be hybridized to the target nucleic acid using a primer that has been labeled with a labeling dye in advance, instead of a terminator.

In addition, a peptide nucleic acid (PNA) may also be used as a probe. The PNA is a nucleic acid in which a pentose-phosphate skeleton, which is the basic skeleton structure of a nucleic acid, has been substituted with a polyamide skeleton including glycine as a unit, and thus has a three-dimensional structure very similar to that of a nucleic acid, and binds very specifically and strongly to a nucleic acid having a complementary base sequence. Accordingly, the PNA may be used for not only existing DNA analysis methods such as in-situ hybridization method, but also as a reagent for telomere research by applying the PNA to a telomere PNA probe.

For example, the detection may be carried out by contacting double-stranded DNA with a PNA having base sequence(s) complementary to all or a part of the base sequence of DNA and having been labeled with a labeling dye for hybridization, heating the mixture to form single-stranded DNA, cooling the mixture slowly to room temperature to prepare a PNA-DNA complex, and measuring the fluorescence thereof.

In the aforementioned example, a method for measuring fluorescence of a product by amplifying the target nucleic acid by the PCR method has been described, but in this method, the amount of the amplified product needs to be examined by confirming the size of the product by electrophoresis and then measuring fluorescence intensity.

For this purpose, the amount of the product may also be measured in real time using a probe which is designed to generate fluorescence by utilizing energy transfer of the fluorescence dye and hybridizing the target nucleic acid with the product of the PCR method.

For example, DNA labeled with a donor and an acceptor may be used. Examples of a specific detection method include a molecular beacon method of confirming the presence of a nucleic acid having a specific sequence, a TaqMan-PCR method, a cycling probe method, and the like.

Further, when a protein is to be detected, a staining dye is used to detect the protein after electrophoresis.

Typically, a method is used in which a staining dye, for example, Coomassie Brilliant Blue (CBB) is penetrated into the gel after electrophoresis to stain the protein, and the protein is irradiated with UV to emit light.

However, although a method of using a staining dye in the related art is easy, sensitivity is low, about 100 ng, so that the method is not suitable for detecting a trace amount of protein. Further, there is also a problem in that a lot of time is required for staining because the staining dye is penetrated through the gel.

In this regard, in the present invention, proteins are labeled by subjecting the proteins to size separation by electrophoresis, and then binding a labeling dye to the separated proteins.

Since the labeling dye of the present invention has a reactive group, reacts quickly and quantitatively with proteins, and furthermore, has high sensitivity, the labeling dye of the present invention is suitable for detecting a trace amount of protein. Furthermore, the size-separated proteins may also be identified by mass spectrometry.

Here, as the protein, it is possible to employ any of simple proteins such as albumin, globulin, glutelin, histone, protamine, and collagen, and complex proteins such as a nucleoprotein, a glycoprotein, a riboprotein, a phosphoprotein, and a metalloprotein as an object to be detected.

For example, a phosphoprotein, a glycoprotein and total protein may be stained in protein samples separated by two-dimensional electrophoresis using three labeling dyes corresponding to the staining dyes of a phosphoprotein, a glycoprotein and total protein.

Further, since proteins may be identified by mass spectrometry such as TOF-Mass, mass spectrometry may be applied to diagnosis or treatment of diseases such as cancer or infectious diseases caused by viruses, producing special proteins.

In addition, collagen is a protein constituting an animal connective tissue and has a unique fiber-shaped structure. That is, collagen consists of a triple polypeptide chain, and the peptide chains gather to form a triple chain. Collagen is generally a protein with very low immunogenicity, and is widely used in fields such as food, cosmetics, and pharmaceuticals.

Further, an aptamer may also be used for the probe. Since the aptamer consists of oligonucleotides and may have various characteristic three-dimensional structures depending on the base sequence, the aptamer may bind to all biomolecules including proteins through the three-dimensional structure. An aptamer labeled with a labeling dye can be bound to a specific protein, and a sample may be indirectly detected from a change in fluorescence according to a structural change of the protein caused by the binding to the sample by binding an aptamer labeled with a labeling dye using these properties.

Other Detection Methods

In addition, the labeling dye of the present invention may also be used in a method for detecting a biomolecule using specific binding.

That is, in the detection of a sample consisting of a biomolecule or a sample modified with a modifying material, either a binding material which specifically binds to the sample or a binding material which specifically binds to the modifying material may be labeled with a labeling dye, and fluorescence from the labeled binding material may be measured.

Here, antigen-antibody, hapten-anti-hapten antibody, biotin-avidin, Tag-anti Tag antibody, lectin-glycoprotein or hormone-receptor may be used for the combination of the sample or modifying material and the binding material.

Specifically, a specific antigen may be detected through the antigen-specific interaction of the antibody by reacting a binding material such as an antibody labeled with a labeling dye with an antigen present on a substrate, in a solution, on a bead or an antibody.

As the antigen, proteins, polysaccharides, nucleic acids, peptides and the like can be used, and in addition to the antigen, a hapten such as FITC or a low molecular weight molecule such as a dinitrophenyl group can also be used. In this case, examples of a combination of the antigen (or hapten) and the antibody include GFP and anti-GFP antibody, FITC and anti-FITC antibody, and the like.

Labeled antigens may be used for various measurement methods such as immunostaining, ELISA, Western blotting, and flow cytometry.

Further, an intracellular signaling phenomenon may also be observed using the labeling dye of the present invention. Various enzymes and the like are involved in internal signaling or a reaction of a cell associated therewith. It is known that in a representative signaling phenomenon, a special protein kinase is activated, and accordingly, protein phosphorylation is induced, and as a result, signaling is initiated.

The binding and hydrolysis of nucleotides (for example, ATP or ADP) play a crucial role in their activity, and an intracellular signaling phenomenon may be observed with high sensitivity by introducing a labeling dye into a nucleotide derivative.

Further, the labeling dye of the present invention may also be used for observing gene expression phenomena using RNA interference (RNAi).

RNAi suppresses the expression of a target gene by introducing double-stranded RNA (dsRNA) into cells to degrade the mRNA of the target gene, and the RNAi phenomenon can be observed by labeling the designed dsRNA with a labeling dye.

In addition, the labeling dye of the present invention may be used as a dye for confirming the transcription level of a target nucleic acid or the expression level of a target protein by including a reactive group capable of labeling the target nucleic acid or target protein in tissues or cells.

PREPARATION EXAMPLES

Preparation Example 1: Preparation of Compound 1

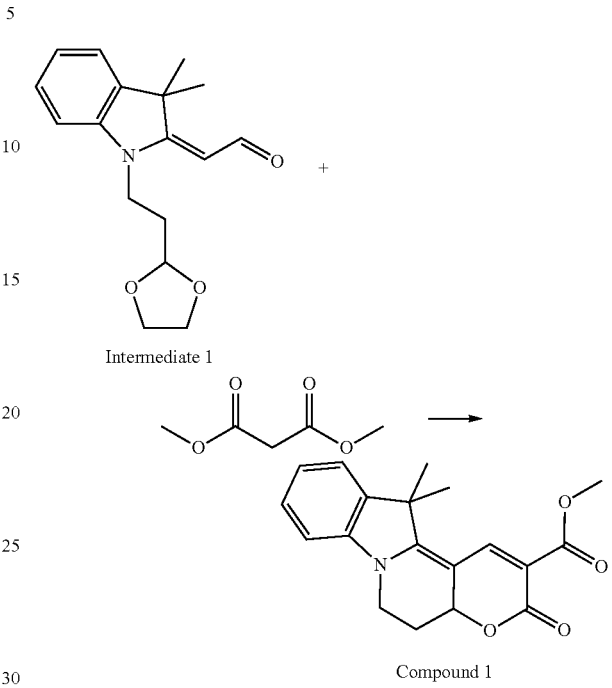

After 5.0 g of Intermediate 1 (Nucleic Acids Research, 40(14), e108; 2012 and Tetrahedron, 41(22), 5341; 1985), 6.9 g of dimethyl malonate, 3.0 g of piperidine, and 100 mL of methanol were introduced and the resulting mixture was stirred under reflux for 24 hours and concentrated under reduced pressure, chloroform and a 50% aqueous sulfuric acid solution were added thereto, and the resulting mixture was stirred for 1 hour. Thereafter, the organic layer was extracted with methylene chloride, concentrated under reduced pressure, and purified with silica gel column chromatography to prepare Compound 1 (1.5 g, MS (ESI): m/z 326.2).

Preparation Example 2: Preparation of Compounds 2 and 3

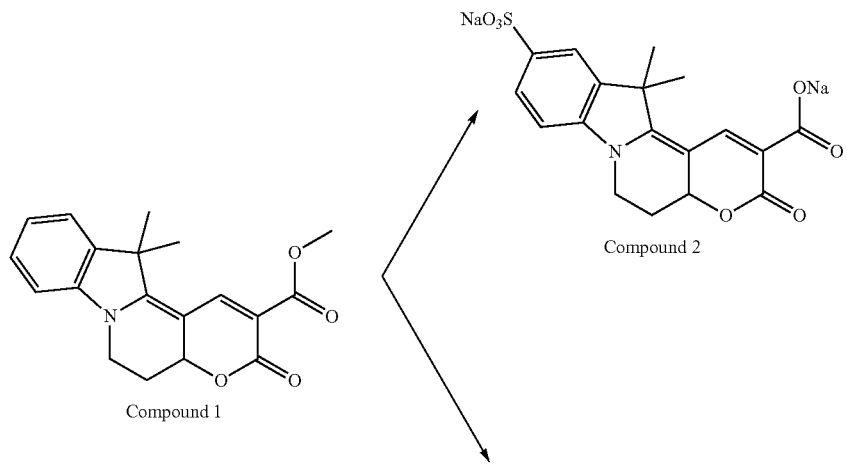

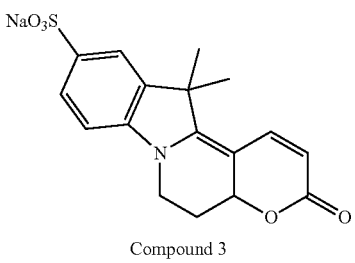

Compound 3

After 400 mg of Compound 1 and 8 mL of sulfuric acid were introduced into a reactor and then stirred for 48 hours, the resulting mixture was cooled to 0° C., neutralized with an aqueous sodium hydroxide solution, and then filtered. The filtrate was concentrated under reduced pressure and purified with ODS column chromatography to prepare Compound 2 (122 mg, MS (ESI): m/z 389.8) and Compound 3 (30 mg, MS (ESI): m/z 346.2).

Preparation Example 3: Preparation of Compound 4

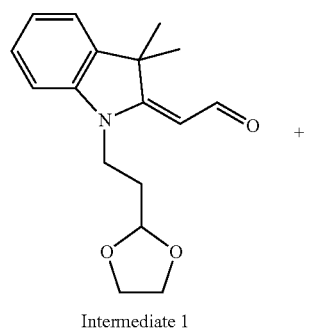

Intermediate 1

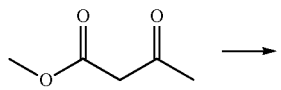

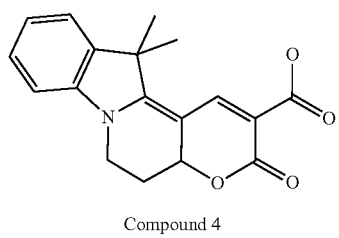

Compound 4

After 5.0 g of Intermediate 1 (Nucleic Acids Research, 40(14), e108; 2012 and Tetrahedron, 41(22), 5341; 1985), 6.9 g of dimethyl malonate, 3.0 g of piperidine, and 100 mL of methanol were introduced and the resulting mixture was stirred under reflux for 24 hours and concentrated under reduced pressure, chloroform and a 50% aqueous sulfuric acid solution were added thereto, and the resulting mixture was stirred for 1 hour. Thereafter, the organic layer was extracted with methylene chloride, concentrated under reduced pressure, and purified with silica gel column chromatography to prepare Compound 4 (1.5 g, MS (ESI): m/z 310.2).

Preparation Example 4: Preparation of Compound 5

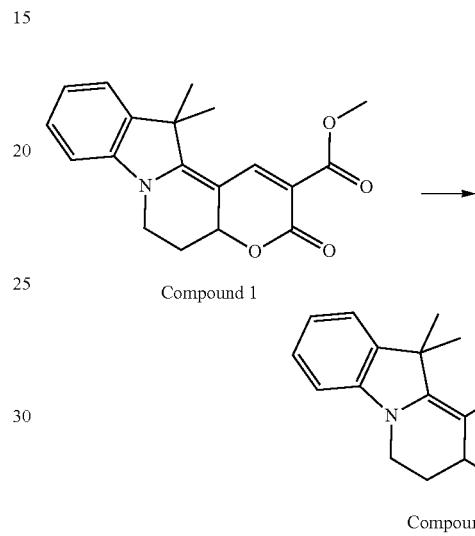

Compound 1

Compound 5

After 300 mg of Compound 1 and 240 mg of sodium hydroxide, 5 mL of methanol, and 5 mL of water were introduced and then stirred for 12 hours, the resulting mixture was cooled to 0° C. and neutralized with an aqueous hydrochloric acid solution. Thereafter, the organic layer was extracted with methylene chloride, concentrated under reduced pressure, and purified with silica gel column chromatography to prepare Compound 5 (120 mg, MS (ESI): m/z 312.1).

Preparation Example 5: Preparation of Compound 6

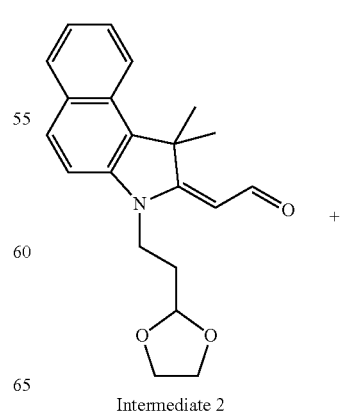

Intermediate 2

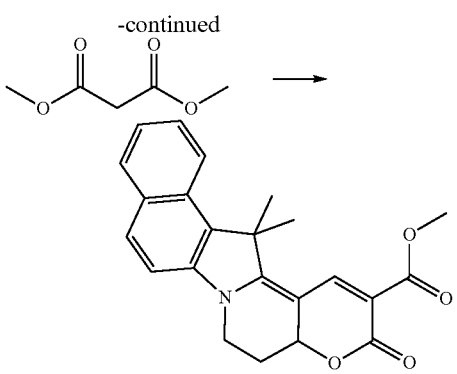

Compound 6

After 5.0 g of Intermediate 2 (Nucleic Acids Research, 40(14), e108; 2012 and Tetrahedron, 41(22), 5341; 1985), 6.9 g of dimethyl malonate, 3.0 g of piperidine, and 100 mL of methanol were introduced and the resulting mixture was stirred under reflux for 24 hours and concentrated under reduced pressure, chloroform and a 50% aqueous sulfuric acid solution were added thereto, and the resulting mixture was stirred for 1 hour. Thereafter, the organic layer was extracted with methylene chloride, concentrated under reduced pressure, and purified with silica gel column chromatography to prepare Compound 6 (1.5 g, MS (ESI): m/z 376.2).

Preparation Example 6: Preparation of Compounds 7 and 8

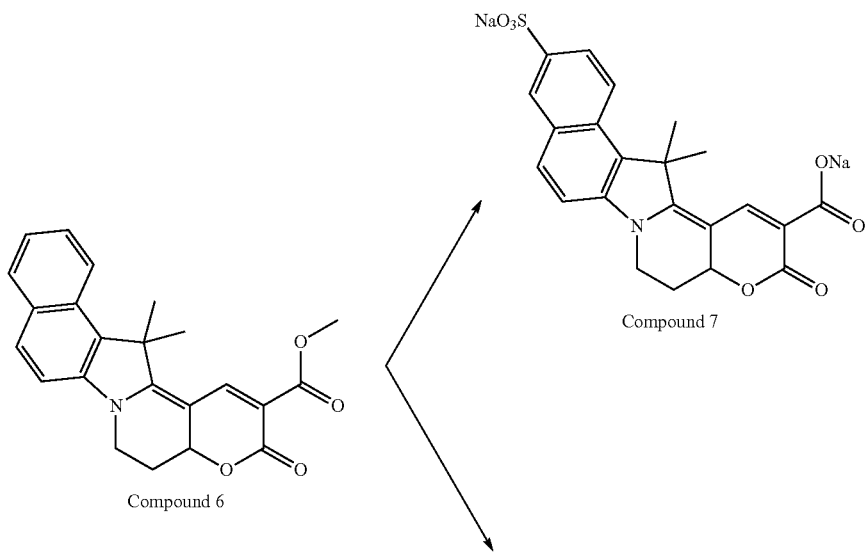

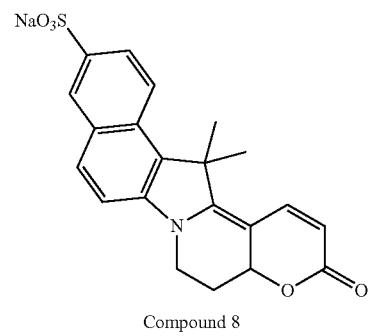

Compound 8

After 400 mg of Compound 6 and 8 mL of sulfuric acid were introduced into a reactor and then stirred for 48 hours, the resulting mixture was cooled to 0° C., neutralized with an aqueous sodium hydroxide solution, and then filtered. The filtrate was concentrated under reduced pressure and purified with ODS column chromatography to prepare Compound 7 (122 mg, MS (ESI): m/z 439.7) and Compound 8 (30 mg, MS (ESI): m/z 395.8).

Preparation Example 7: Preparation of Compound 65

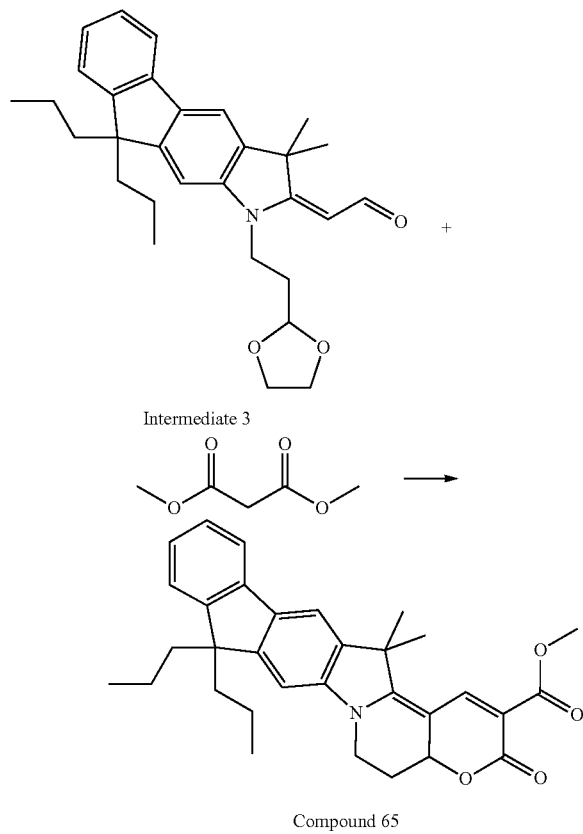

Compound 65

Compound 65 (0.4 g, MS (ESI): m/z 442.2) was prepared in the same manner as in Preparation Example 1, except that Intermediate 3 (Dyes and Pigments (2014), 101, 1-8, Nucleic Acids Research, 40(14), e108; 2012 and Tetrahedron, 41(22), 5341; 1985) was prepared instead of Intermediate 1 in Preparation Example 1.

Experimental Example 1

For each compound obtained in Preparation Examples 1 to 7, the absorption spectrum, light emission spectrum, molecular extinction coefficient, and quantum efficiency were measured and are shown in the following Table 1.

TABLE 1

| Classification | Solvent | $\lambda_{ex}$ (nm) | $\lambda_{em}$ (nm) | ε (Lmol$^{-1}$cm$^{-1}$) | φ |
|---|---|---|---|---|---|
| Compound 1 | DMSO | 456 | 479 | 63,000 | 0.900 |
| Compound 2 | PBS | 451 | 487 | 44,000 | 0.796 |

TABLE 1-continued

| Classification | Solvent | $\lambda_{ex}$ (nm) | $\lambda_{em}$ (nm) | ε (Lmol$^{-1}$cm$^{-1}$) | φ |
|---|---|---|---|---|---|
| | H$_2$O | 453 | 489 | 45,000 | 0.718 |
| | DMSO | 468 | 500 | 30,000 | 0.768 |
| | MeOH | 463 | 493 | 50,000 | 0.625 |
| | CH$_2$Cl$_2$ | 429 | 495 | 20,000 | 0.169 |
| Compound 3 | PBS | 423 | 492 | 28,000 | 0.759 |
| | H$_2$O | 423 | 492 | 28,000 | 0.764 |
| | DMSO | 416 | 470 | 27,000 | 0.645 |
| | MeOH | 410 | 484 | 27,000 | 0.667 |
| | CH$_2$Cl$_2$ | 403 | 464 | 22,000 | 0.227 |
| Compound 4 | DMSO | 492 | 516 | 47,000 | 0.910 |
| Compound 5 | PBS | 454 | 483 | 49,000 | 0.633 |
| | H$_2$O | 452 | 483 | 50,000 | 0.062 |
| | DMSO | 466 | 490 | 49,000 | 0.913 |
| | EtOH | 462 | 485 | 51,000 | 0.412 |
| Compound 6 | DMSO | 474 | 503 | 53,000 | 0.928 |
| Compound 7 | H$_2$O | 470 | 502 | 45,000 | 0.649 |
| | DMSO | 486 | 517 | 43,000 | 0.788 |
| | EtOH | 482 | 511 | 47,000 | 0.587 |
| Compound 8 | DMSO | 442 | 480 | 32,000 | 0.767 |
| Compound 9 | DMSO | 492 | 516 | 47,000 | 0.910 |
| Compound 16 | DMSO | 494 | 519 | 47,000 | 0.935 |
| | PBS | 492 | 516 | 51,000 | 0.417 |
| | H$_2$O | 492 | 516 | 48,000 | 0.405 |
| | EtOH | 490 | 516 | 47,000 | 0.872 |
| | CH$_2$Cl$_2$ | 488 | 515 | 49,000 | 0.137 |
| Compound 60 | DMSO | 476 | 513 | 42,000 | — |
| | H$_2$O | 476 | 523 | 38,000 | — |
| | EtOH | 474 | 519 | 42,000 | — |
| | CH$_2$Cl$_2$ | 470 | 511 | 41,000 | — |
| Compound 61 | DMSO | 480 | 525 | 47,000 | — |
| | PBS | 468 | 518 | 46,000 | — |
| | H$_2$O | 468 | 516 | 46,000 | — |
| | EtOH | 480 | 525 | 49,000 | — |
| | CH$_2$Cl$_2$ | 484 | 522 | 46,000 | — |
| Compound 62 | DMSO | 492 | 516 | 46,000 | 0.958 |
| | PBS | 486 | 520 | 29,000 | 0.193 |
| | H$_2$O | 468 | 520 | 26,000 | 0.194 |
| | EtOH | 486 | 516 | 47,000 | 0.820 |
| | CH$_2$Cl$_2$ | 486 | 511 | 42,000 | 0.944 |
| Compound 63 | DMSO | 416 | 470 | 15,000 | — |
| | PBS | 434 | 507 | 17,000 | — |
| | H$_2$O | 432 | 506 | 17,000 | — |
| | EtOH | 416 | 485 | 15,000 | — |
| | CH$_2$Cl$_2$ | 414 | 466 | 15,000 | — |
| Compound 64 | DMSO | 412 | 472 | 26,000 | 0.84 |
| | PBS | 423 | 503 | 27,000 | 0.95 |
| | H$_2$O | 422 | 500 | 26,000 | 0.91 |
| | EtOH | 408 | 483 | 28,000 | 0.78 |
| | CH$_2$Cl$_2$ | 414 | 468 | 22,000 | 0.01 |

As shown in Table 1, merocyanine-based compounds according to various exemplary embodiments of the present invention may be dissolved in various solvents to exhibit high extinction coefficients and quantum efficiencies and emit fluorescence signals at a visible light wavelength region of at least of 380 nm.

Experimental Example 2

After a 1 mg/ml protein solution was prepared by diluting Goat Anti-Mouse IgG with a 0.1 M sodium bicarbonate buffer, 125 µl of the protein solution was added to each of 8 tubes. A dye solution (5 mg/ml) including Compound 2 prepared according to Preparation Example 2 was added to prepared tubes at 1, 2, 3, 5, 7, 9, 11, and 13 µl, and the tubes were immediately vortexed. Subsequently, after the dye solutions were shaken at room temperature in a locker for 30 minutes, the reaction solutions were added to Amicon centrifuge filters. The reaction solutions were filtered with PBS until the free dye was removed by a centrifuge (14,000 rpm, 10 minutes, 5 times).

After inverting and binding the centrifuge filter to an Amicon tube, the filtrate was recovered (1000 rpm, 2 minutes) and then diluted with 1 ml of PBS, and then fluorescence was measured by UV, PL and a microplate reader.

The ratio of the dye to the protein was determined using the following equation.

$$\frac{D}{P} = \frac{A_{dye} \times E_{prot}}{(A_{280} - XA_{dye}) \times E_{dye}}$$

Figure 2:
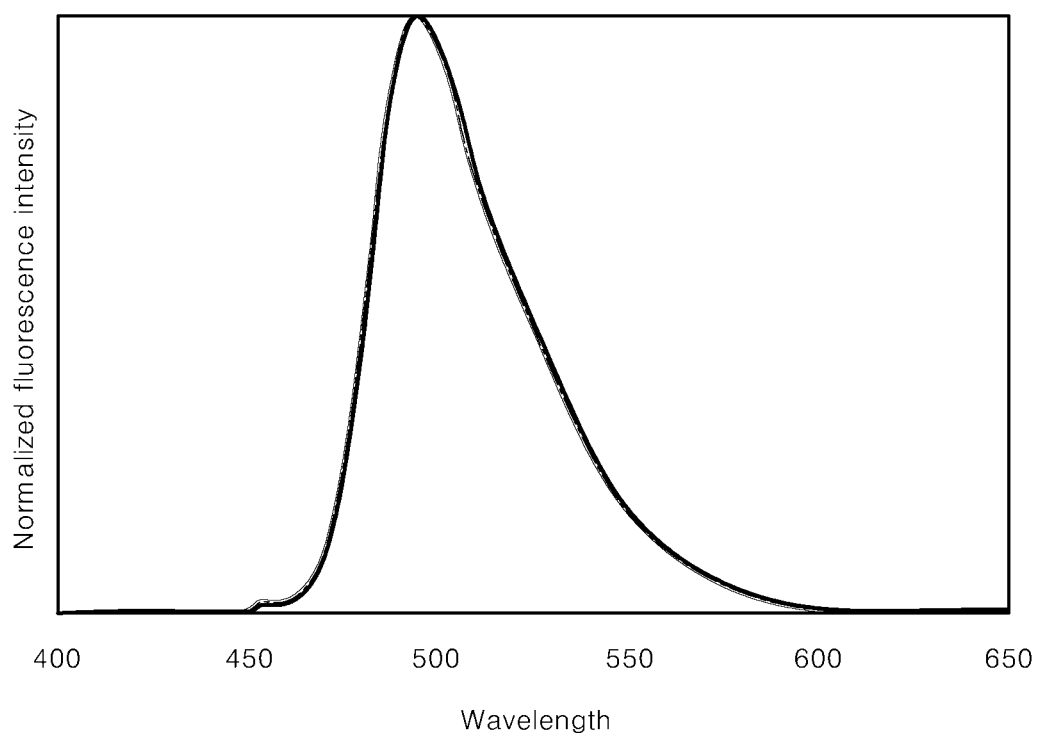
FIG. 2 is a fluorescence emission spectrum after labeling Goat Anti-Mouse IgG with a merocyanine-based compound (Compound 2) according to an exemplary embodiment of the present invention.
Figure 3:
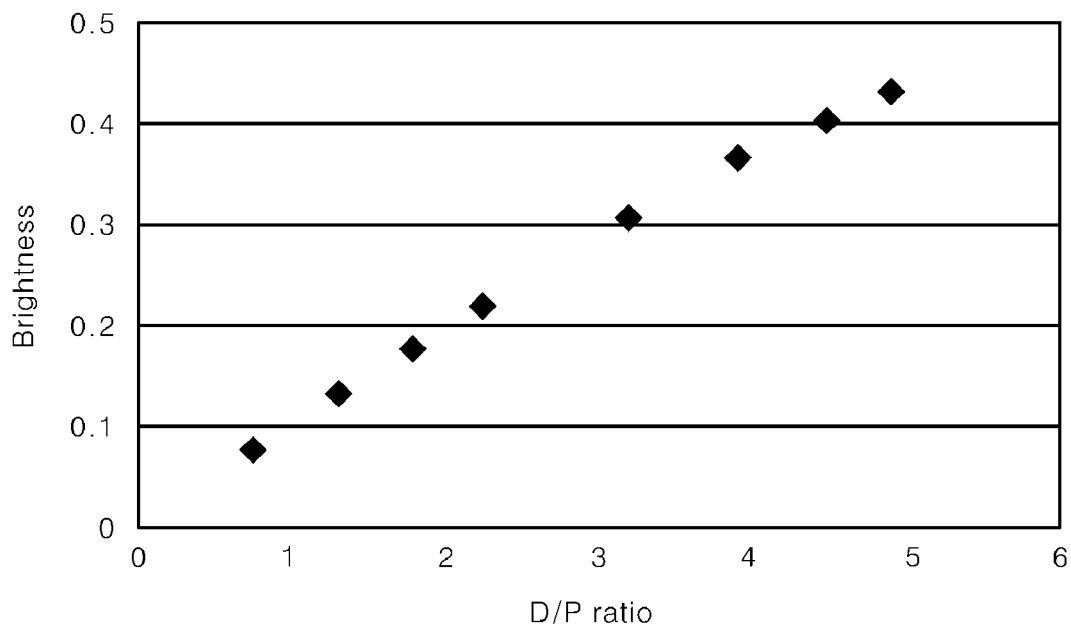
FIG. 3 is a brightness spectrum after labeling Goat Anti-Mouse IgG with a merocyanine-based compound (Compound 2) according to an exemplary embodiment of the present invention.

$A_{dye}$: Absorbance of dye at maximum absorption wavelength after labeling $A_{280}$: Absorbance at 280 nm $E_{prot}$: Molecular extinction coefficient (210,000 in the case of IgG) of protein at 280 nm $E_{dye}$: Molecular extinction coefficient of dye at maximum absorption wavelength X: Absorbance at 280 nm/absorbance of Compound 2 at maximum absorption wavelength After Goat Anti-Mouse IgG is labeled with Compound 2, referring to FIGS. 1 to 3 illustrating the spectra, the spectrum pattern after labeling can be confirmed, and it can be confirmed that as the D/P ratio is increased from 1 to 5, the brightness is increased.

Experimental Example 3

After a 1 mg/ml protein solution was prepared by diluting Goat Anti-Mouse IgG with a 0.1 M sodium bicarbonate buffer, 125 µl of the protein solution was added to each of 7 tubes. A dye solution (5 mg/ml) including Compound 7 prepared according to Preparation Example 6 was added to prepared tubes at 1, 2, 3, 4, 5, 6, and 7 µl, and the tubes were immediately vortexed. Subsequently, after the dye solutions were shaken at room temperature in a locker for 30 minutes, the reaction solutions were added to Amicon centrifuge filters. The reaction solutions were filtered with PBS until the free dye was removed by centrifuge (14,000 rpm, 10 minutes, 5 times).

After inverting and binding the centrifuge filter to an Amicon tube, the filtrate was recovered (1000 rpm, 2 minutes) and then diluted with 1 ml of PBS, and then fluorescence was measured by a microplate reader.

Figure 4:
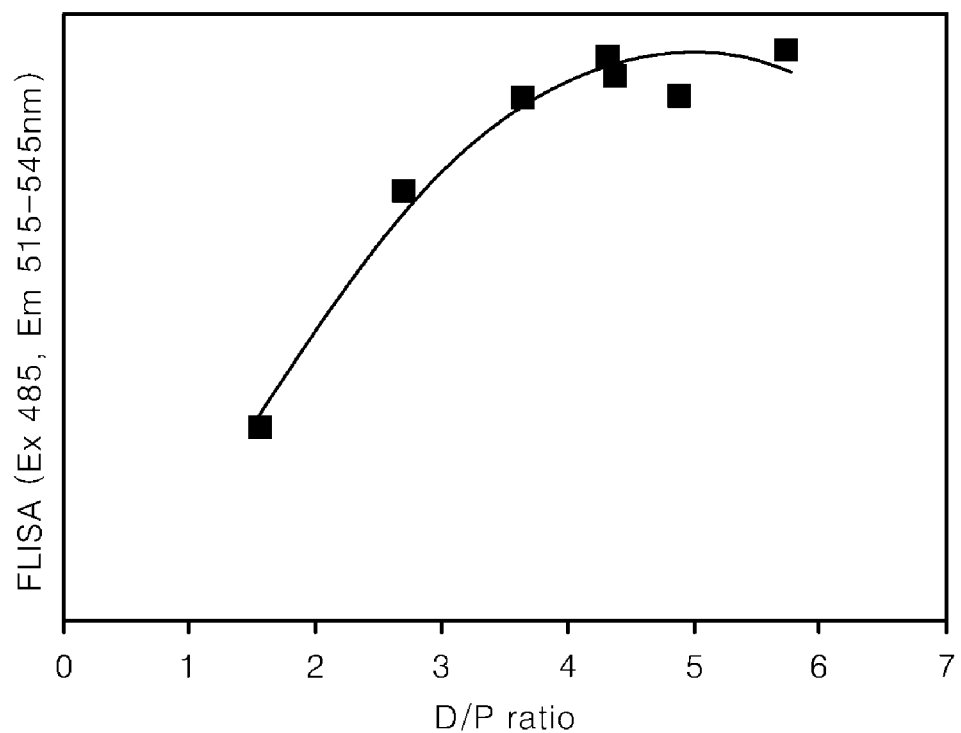
FIG. 4 is a brightness spectrum after labeling Goat Anti-Mouse IgG with a merocyanine-based compound (Compound 7) according to another exemplary embodiment of the present invention.

After Goat Anti-Mouse IgG is labeled with Compound 7, referring to FIG. 4 illustrating the brightness spectrum, it can be confirmed that when the D/P ratio is 6, maximum brightness is exhibited.

As described above, exemplary embodiments of the present invention have been described, but it should be understood that a person with ordinary skill in the art may modify and change the present invention in various ways within the range not departing from the spirit of the present invention described in the claims by the addition, change, or deletion of constituent elements, and that the modifications and changes are included in the scope of the present invention.

The invention claimed is:

1. A merocyanine-based compound represented by the following Chemical Formula 1:

[Chemical Formula 1]

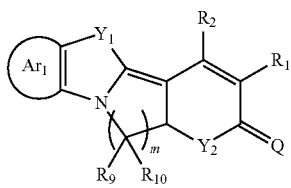

wherein, $Ar_1$ is a substituted or unsubstituted aryl or a substituted or unsubstituted heteroaryl, $Y_1$ and $Y_2$ are each independently selected from sulfur, oxygen, selenium, $NR_3$, $CR_3R_4$, $SiR_3R_4$, and $-CR_3=CR_4-$, Q is sulfur, oxygen, or $NR_a$, $R_1$ is each independently selected from hydrogen, deuterium, a substituted or unsubstituted $C_1$-$C_{10}$ alkyl, a substituted or unsubstituted $C_2$-$C_{10}$ alkenyl, a substituted or unsubstituted $C_1$-$C_{10}$ haloalkyl, a halogen, cyano, a substituted or unsubstituted amino, a substituted or unsubstituted amide, carboxyl, carboxylates, a substituted or unsubstituted aryl, a substituted or unsubstituted heteroaryl, ketones ($-COR_5$), aldehydes, esters ($-COOR_5$), a -L-X functional group, and a -L-Z functional group, $R_a$ and $R_2$ to $R_4$ are each independently selected from hydrogen, deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, sulfhydryl, nitro, carboxyl, carboxylates, a substituted or unsubstituted aryl, a substituted or unsubstituted heteroaryl, a substituted or unsubstituted aralkyl, quaternary ammonium, phosphoric acid, phosphates, ketones ($-COR_5$), aldehydes, esters ($-COOR_5$), acyl chloride, sulfonic acid, sulfonates, a -L-X functional group, and a -L-Z functional group, when $R_1$, $R_2$, $R_3$, or $R_4$ is a ketone group ($-COR_5$) or an ester group ($-COOR_5$), $R_5$ is selected from a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted $C_1$-$C_{10}$ haloalkyl, a substituted or unsubstituted heteroaryl, and a substituted or unsubstituted $C_1$-$C_{10}$ aminoalkyl, $R_9$ and $R_{10}$ are each independently selected from hydrogen and a substituted or unsubstituted alkyl, or $R_9$ and $R_{10}$ are bonded to each other to form a four-membered, five-membered, or a six-membered hydrocarbon ring, in the -L-X and -L-Z functional groups, L is a linker selected from 1-20 atoms selected from carbon, nitrogen, oxygen, and sulfur, $-NHCOO-$, $-CONH-$, $-CH_2NH-$, $-CH_2NR_6-$, $-COO-$, $-SO_2NH-$, $-HN-C(=NH)-NH-$, $-NR_6-$, $-(CH_2-CH_2-O-)_p-$, $-CH=CH-$, $-C\equiv C-$, $-Ar-$, and $-CO-Ar-NR_6-$, $R_6$ is selected from hydrogen, a substituted or unsubstituted $C_1$-$C_6$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_6$ alkoxy, and a substituted or unsubstituted $C_1$-$C_6$ haloalkyl, Ar is an aryl or a heteroaryl, and p is an integer from 1 to 100, X is a reactive group selected from carboxyl, succinimidyl ester, sulfo-succinimidyl ester, isothiocyanate, maleimide, haloacetamide, hydrazide, vinyl sulphone, dichlorotriazine, phosphoramidite, alkyl halides, acyl halides, carbohydrazide, hydroxylamine, ketones, alkynes, azide, aliphatic and aromatic amines, sulfotetrafluorophenyl ester, sulfodichlorophenyl ester, carbonyl azide, sulfonyl chloride, sulfonyl fluoride, boronic acid, isocyanate, a halogen-substituted triazine, a halogen-substituted pyridine, a halogen-substituted diazine, tetrafluorophenyl ester, imido ester, azidonitrophenyl, glyoxal, and aldehydes, Z is a fluorophore capable of generating a fluorescence signal, when $R_1$, $R_2$, $R_3$, $R_4$, $R_5$, or $R_6$ is substituted, any carbon or terminal carbon in the functional group is substituted with at least one selected from sulfonic acid, sulfonates, carboxylic acids, carboxylates, phosphoric acid, phosphates, alkyls, heteroaryls, polyalkylene oxides, quaternary ammonium salts, esters, and amides, and m is an integer from 1 to 3.

2. The merocyanine-based compound of claim 1, wherein when $Ar_1$ is substituted, any carbon in the functional group is substituted with at least one selected from deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, nitro, a substituted or unsubstituted sulfonamide, polyalkylene oxides, carboxyl, carboxylates, a substituted or unsubstituted aryl, a substituted or unsubstituted heteroaryl, a substituted or unsubstituted aralkyl, quaternary ammonium, phosphoric acid, phosphates, ester (—$COOR_5$), acyl chloride, sulfonic acid, sulfonates, a -L-X functional group, and a -L-Z functional group.

3. The merocyanine-based compound of claim 1, wherein Z is a fluorophore selected from structures displayed by coumarins, cyanine, BODIPY, fluoresceins, rhodamines, pyrenes, carbopyronin, oxazines, xanthenes, thioxanthene, acridines, and Chemical Formula 1.

4. The merocyanine-based compound of claim 1, wherein the merocyanine-based compound is at least one selected from compounds represented by the following Chemical Formulae:

[Chemical Formula 2]

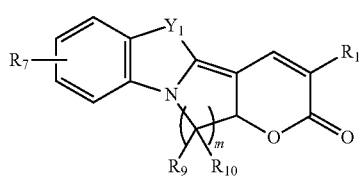

[Chemical Formula 3]

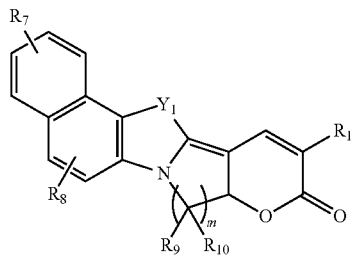

[Chemical Formula 4]

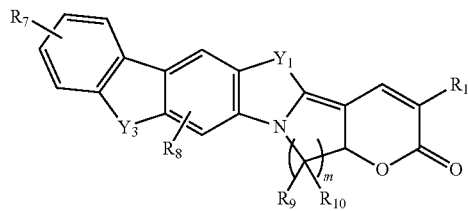

wherein, $R_7$ and $R_8$ are each independently selected from hydrogen, deuterium, a substituted or unsubstituted $C_1$-$C_{10}$ alkyl, a substituted or unsubstituted $C_2$-$C_{10}$ heteroalkyl including at least one heteroatom, a substituted or unsubstituted $C_2$-$C_{10}$ alkenyl, a substituted or unsubstituted $C_2$-$C_{10}$ alkynyl, a substituted or unsubstituted $C_2$-$C_{10}$ alkoxy, a substituted or unsubstituted aryloxy, a substituted or unsubstituted $C_1$-$C_{10}$ haloalkyl, a halogen, cyano, hydroxyl, a substituted or unsubstituted amino, a substituted or unsubstituted amide, carbamates, nitro, a substituted or unsubstituted sulfonamide, polyalkylene oxides, carboxyl, carboxylates, a substituted or unsubstituted aryl, a substituted or unsubstituted heteroaryl, a substituted or unsubstituted aralkyl, quaternary ammonium, phosphoric acid, phosphates, ester (—$COOR_5$), acyl chloride, sulfonic acid, sulfonates, a -L-X functional group, and a -L-Z functional group, and $Y_3$ is sulfur, oxygen, selenium, $NR_3$, $CR_3R_4$, $SiR_3R_4$, or —$CR_3$=$CR_4$—.

5. A biomolecular labeling dye comprising the merocyanine-based compound according to claim 1.

6. The biomolecular labeling dye of claim 5, wherein the biomolecular labeling dye is used to label at least one selected from antibodies, lipids, proteins, peptides, carbohydrates, and nucleic acids.

7. A biomolecular labeling kit comprising the biomolecular labeling dye according to claim 6.

8. A contrast agent composition comprising the merocyanine-based compound according to claim 1.

* * * * *